US006908617B1

(12) United States Patent
Wyatt et al.

(10) Patent No.: US 6,908,617 B1
(45) Date of Patent: Jun. 21, 2005

(54) GLYCOSYLATED MODIFIED PRIMATE LENTIVIRUS ENVELOPE POLYPEPTIDES

(75) Inventors: Richard T. Wyatt, Andover, MA (US); Joseph G. Sodroski, Medford, MA (US); Peter D. Kwong, New York, NY (US); Wayne A. Hendrickson, Hastings on Hudson, NY (US)

(73) Assignees: Dana-Farber Cancer Institute, Inc., Boston, MA (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/446,799

(22) PCT Filed: Nov. 10, 1998

(86) PCT No.: PCT/US98/23998

§ 371 (c)(1),
(2), (4) Date: May 1, 2001

(87) PCT Pub. No.: WO99/24464

PCT Pub. Date: May 20, 1999

Related U.S. Application Data

(63) Continuation-in-part of application No. 09/100,764, filed on Jun. 18, 1998, and a continuation-in-part of application No. 09/100,529, filed on Jun. 18, 1998, and a continuation-in-part of application No. 09/100,763, filed on Jun. 18, 1998, and a continuation-in-part of application No. 09/100,521, filed on Jun. 18, 1998, and a continuation-in-part of application No. 09/100,631, filed on Jun. 18, 1998, and a continuation-in-part of application No. 09/100,762, filed on Jun. 18, 1998, and a continuation-in-part of application No. 08/976,741, filed on Nov. 24, 1997, and a continuation-in-part of application No. 08/966,987, filed on Nov. 10, 1997, and a continuation-in-part of application No. 08/967,403, filed on Nov. 10, 1997, and a continuation-in-part of application No. 08/967,708, filed on Nov. 10, 1997, and a continuation-in-part of application No. 08/967,148, filed on Nov. 10, 1997, and a continuation-in-part of application No. 08/966,932, filed on Nov. 10, 1997.

(60) Provisional application No. 60/089,581, filed on Nov. 10, 1997, and provisional application No. 60/089,580, filed on Nov. 10, 1997.

(51) Int. Cl.[7] .................. A61K 19/00; A36K 36/16; C07K 19/00; C12P 21/00

(52) U.S. Cl. .................. 424/207.1; 424/205.1; 424/208.1; 530/350; 530/302; 530/323; 435/69.1

(58) Field of Search .................. 424/205.1, 207.1, 424/208.1; 530/300, 323

(56) References Cited

U.S. PATENT DOCUMENTS 5,817,316 A    10/1998  Thali .................. 424/188.1

FOREIGN PATENT DOCUMENTS

WO    093/17705 A1 *  9/1993

OTHER PUBLICATIONS

Lekutis et al. Journal of Acquired Immune Deficiency Syndromes 1992, vol. 5, pp. 78–81.*
Lee et al. P.N.A.S. USA 1992, vol. 89, pp. 2213–2217.*
Bolmstedt et al. J. Gene Virol. 1991, vol. 72, pp. 1269–1277.*
Alkhatib, G., et al., Science 272:1955–1958 (1996).
Allan, JS., et al., Science 228:1091–1093 (1985).
Altschul, SF., et al., Nucleic Acids Res. 25:3389–3402 (1997).
Arendrup, et al., J. AIDS 5:303–307 (1992).
Arthos, J., et al., Cell 57:469 (1989).
Baggioline, M., et al., Adv. Immunol. 55:97–179 (1994).
Barre–Sinousi, F., et al., Science 220:868–871 (1983).
Berkower, et al., J. Exp. Med. 170:1681–1695 (1989).
Berman, PW., et al., Nature 345:622–625 (1990).
Binley, J., et al., AIDS Res. Hum. Retroviruses, 14:191–198 (1997).
Bolmstedt, A., et al., J. AIDS 12:213–220 (1996).
Brodsky, MH., et al., J Immunol. 144:3078–3086 (1990 ).
Bruck, et al., Vaccine 12:1141–1148 (1994).
Bullough, P., et al., Nature 371:37–43 (1994).
Burton, et al., Science 266:1024–1027 (1994).
Cao, J., et al., J. Virol. 71:9808–9812 (1997).
Carr, CM., et al., Cell 73:823–832 (1993).
Chan, DC., et al., Cell 89:263–273 (1997).
Chen, CH., et al., J. Virol. 69:3771–3777 (1995).
Chen, Z., et al., J. Virol. 71:2705–2714 (1997).
Cheng–Mayer, C., et al., Science 240:80–82 (1988).
Choe, H., et al., Cell 85:1135–1148 (1996).
Clark, SJ, et al., N. Engl. J. Med. 324:950–960 (1991).
Cocchi, F., et al., Nature Med. 2:1244–1247 (1996).
Cocchi, F., et al., Science 270:1811–1815 (1995).
Connor, R., et al., J. Exp. Med. 185:628 (1997).
Connor, RI., et al., J. Virol. 67:1772–1778 (1993).
Coombs, RW., et al., N. Engl. J. Med. 321:1626–1631 (1989).
Cordonnier, A., et al., Nature 340:571–574 (1989).
D'Souza, et al., J. Infect. Dis. 175: 1056–1062 (1997).
Daar, ES., et al., N. Engl. J. Med. 324:961–964 (1991).

(Continued)

Primary Examiner—Ali R. Salimi
Assistant Examiner—Bao Qun Li
(74) Attorney, Agent, or Firm—Nixon Peabody LLP

(57) ABSTRACT

A modified polypeptide corresponding to an envelope glycoprotein of a primate lentivirus is described. The polypeptide has been modified from the wild-type structure so that it has at least two of the glycosylation sites proximal to the CD4 binding site or chemokine receptor site altered so that the alteration prevents glycosylation at that site or where glycosylation sites distal to these sites have been derivatized with a molecular adjuvant, while retaining the overall 3-dimensional structure of a discontinuous conserved epitope of the wild-type protein. Preferably, the polypeptide has both changes. Preferably, the primate lentivirus is HIV, and the protein is HIV-1 gp 120.

13 Claims, 7 Drawing Sheets

OTHER PUBLICATIONS

Daar, et al., *Proc. Natl. Acad. Sci.* USA 87:6574–6578 (1990).
Dalgleish, AG., et al., *Nature* 312:763–767 (1984).
Dalum, et al., *Mol. Immunol.* 34:1113–1120 (1997).
Davidson, et al., *Nat. Genet* 3:219 (1993).
Dean, M., et al., *Science* 273:1856–1862 (1996).
Dempsey, P., et al., *Science* 271:348–350 (1996).
Deng, HK., et al., *Nature* 381:661–666 (1996).
Doranz, BJ., et al., *Cell* 85:1149–1158 (1996).
Dragic, T., et al., *Nature* 381:667–673 (1996).
Earl, PL., et al., *J. Virol.* 65:2047–2055 (1991).
Earl, PL., et al., *Proc. Natl. Acad. Sci.* USA 87:648–652 (1990).
Emini, et al., *Nautre* 355:728–730 (1991).
Fauci, AS., et al., *Ann. Inter. Med.* 124:654–663 (1996).
Feng, Y., et al., *Science* 272:872–877 (1996).
Fenyo, E., et al., *J. Virol.* 62:4414–4419 (1988).
Freed, E., et al., *Proc. Natl. Acad. Sci.* USA 87:4650–4654 (1990).
Fung, et al., *J. Virol.* 66:848–856 (1992).
Gallo, RC., et al., *Science* 224:500–503 (1984).
Gegerfelt, et al., *Virology* 185:162–168 (1991).
Geller, AI., et al., *J. Neurochem* 64:487 (1995).
Geller, AI., et al., *Proc Natl. Acad. Sci. U.S.A.* 87:1149 (1990).
Geller, AI., et al., *Proc Natl. Acad. Sci. U.S.A.* 90:7603 (1993).
Gerard, N., et al., *Curr. Opin. Immunol.* 6:140–145 (1994).
Girard, et al., *Proc. Natl. Acad. Sci.* USA 88:542–546 (1991).
Gorny, et al., *J. Virol.* 66:7538–7542 (1992).
Haigwood, et al., *AIDS Res. Hum. Retro.* 6:855–869 (1990).
Haigwood, et al., *J. Virol.* 66:172–182 (1992).
Ho, DD., et al., *N. Engl. J. Med.* 321:1621–1625 (1989).
Ho, et al., *J. Virol.* 65:489–493 (1991).
Javaherian, et al., *Science* 250:1590–1593 (1990).
Kang, et al., *Proc. Natl. Acad. Sci.* USA 88:6171–6175 (1991).
Kaplitt, MG., et al., *Nat. Genet.* 8:148 (1994).
Karlsson, G., et al., *J. Virol.* 71:4218 (1997).
Klaniecki, et al., *AIDS Res. Hum. Retro.* 7:791–798 (1991).
Klatzmann, D., et al., *Nature London* 312:767–68 (1984).
Kowalski, M., et al., *Science* 237:1351–1355 (1987).
Lasky, L., et al., *Cell* 50:975–985 (1987).
LeGal LaSalle, et al., *Science* 259:988 (1993).
Leonard, CK., et al., *J. Biol. Chem.* 265:10373–10382 (1990).
Liu, R., et al., *Cell* 86:367–378 (1996).
Lu, M., et al., *Nature Structural Biol.* 2:1075–1082 (1995).
Marcon, L., et al., *J. Virol.* 71:2522–2527 (1997).
Matthews, et al., *Proc. Nat. Acad. Sci.* USA 83:9707–9713 (1986).
McKeating, et al., *J. Virol.* 67:4932–4944 (1993).
McKeating, et al., *Virology* 190:134–142 (1992).
Moebius, U., et al., *J. Exp. Med.* 176:507–517 (1982).
Moore, et al., *J. Virol.* 69:101–109 (1995).
Moore, et al., *J. Virol.* 67:6136–6151 (1993).
Moore, et al., *J. Virol.* 67:863–875 (1993).
Moore, et al., *J. Virol.* 69:122–133 (1995).
Moore, et al., *J. Virol.* 70:1863–1872 (1996).
Moore, J., et al., *J. Virol.* 68:469–484 (1994).
Moore, J., et al., *J. Virol.* 68:8350–8364 (1994).
Muster, et al., *J. Virol.* 67:6642–6647 (1993).
Myers, G., et al., "Human Retroviruses and AIDS: A Compilation and Analysis of Nucleic Acid and Amino Acid Sequences," *Los Alamos National Laboratory*, (1994).
Nara, et al., *J. Virol.* 64:3779–3791 (1990).
Ohno, et al., *Proc. Natl. Acad. Sci.* USA 88:10726–10729 (1991).
Olshevsky, U., et al., *J. Virol.* 64:5701–5707 (1990).
Peterson, A., et al., *Cell* 54:65–72 (1988).
Pinter, A., et al., *J. Virol.* 63:2674–2679.
Pollard, S., et al., *EMBO J.* 11:585–591 (1992).
Posner, et al., *J. Immunol.* 16:4325–4332 (1991).
Premack, BA., et al., *Nature Medicine* 11:1174–1178 (1996).
Profy, et al., *J. Immunol.* 144:4641–4647 (1990).
Roben, P., et al., *J. Virol.* 68:4821–4828 (1994).
Robey, W., et al., *Proc. Natl. Acad. Sci.* USA 83:7023–7027 (1986).
Robey, WG., et al., *Science* 228:593–595 (1985).
Robinson, J., et al., *AIDS Res. Hum. Retro* 6:567–580 (1990).
Rusche, et al., *Proc. Natl. Acad. Sci.* USA 84:6924–6928 (1987).
Rusche, J., et al., *Proc. Natl. Acad. Sci.* USA 85:3198–3202 (1988).
Ryu, SE., et al., *Nature London* 348:419–425 (1990).
Samson, M., et al., *Nature* 382:722–725 (1996).
Sattentau, Q., et al., *J. Exp. Med.* 174:407–415 (1991).
Sattentau, Q., et al., *J. Virol.* 67:7388–7393 (1993).
Sawyer, et al., *J. Virol.* 67:1342–1349 (1994).
Schuitemaker, H., et al., *J. Virol.* 66:1354–1360 (1991).
Speck, R., et al., *J. Virol.* 71:7136–7139 (1997).
Starcich, BR., et al., *Cell* 45:637–648 (1986).
Steimer, et al., *Science* 254:105–108 (1991).
Sullivan, et al., *J. Virol.* 69:4413–4422 (1995).
Thali, et al., *J. Virol.* 65:6188–6193 (1991).
Thali, et al., *J. Virol.* 66:5635–5641 (1992).
Thali, M., et al., *J. Virol.* 67:3978–3988 (1993).
Tilley, et al., *Res. Virol.* 142:247–259 (1991).
Trkola, A., et al., *J. Virol.* 70:1100–1108 (1996).
Trkola, A., et al., *Nature* 384: 184–187 (1996).
Wang, J., et al., *Nature London* 348:411–418 (1990).
Watkins, B., et al., *J. Virol.* 67:7493 (1993).
Weissenhorn, W., et al., *EMBO J.* 15:1507–1514 (1996).
Weissenhorn, W., et al., *Nature* 387:426–430 (1997).
Wu, L., et al., *Nature* 384:179–183 (1996).
Wyatt, et al., *J. Virol.* 69:5723–5733 (1995).
Wyatt, R., et al., *J. Virol.* 67:4557–4565 (1993).
Wyatt, R., et al., *J. Virol.* 72:9722–9731 (1997).
Yang, et al., *J. Virol.* 69:2004 (1995).
Zhang, L., et al., *Nature* 383:768 (1996).
Zhu, T., et al., *Science* 261:1179–1181 (1993).

* cited by examiner

GLYCOSYLATED MODIFIED PRIMATE LENTIVIRUS ENVELOPE POLYPEPTIDES

This application is a national stage entry under 35 U.S.C. § 371 of international application PCT/US98/24001, filed Nov. 10, 1998, which claimed benefit under 35 U.S.C. § 120 as a continuation-in-part of the following U.S. applications: U.S. Ser. No. 08/966,932, filed Nov. 10, 1997; U.S. Ser. No. 08/967,148, filed Nov. 10, 1997; U.S. Ser. No. 08/967,708, filed Nov. 10, 1997; U.S. Ser. No. 08/967,403, filed Nov. 10, 1997; U.S. Ser. No. 08/966,987, filed Nov. 10, 1997; U.S. Ser. No. 08/976,741, filed Nov. 24, 1997; U.S. Ser. No. 09/100,762, filed Jun. 18, 1998; U.S. Ser. No. 09/100,631, filed Jun. 18, 1998; U.S. Ser. No. 09/100,521, filed Jun. 18, 1998; U.S. Ser. No. 09/100,763, filed Jun. 18, 1998; U.S. Ser. No. 09/100,529, filed Jun. 18, 1998; and U.S. Ser. No. 09/100,764, filed Jun. 18, 1998; and which claimed benefit under 35 U.S.C. §119(e) of U.S. provisional applications 60/089,581, filed Jun. 17, 1998, and U.S. provisional application 60/089,580, filed Jun. 17, 1998.

FIELD OF THE INVENTION

The present invention is directed to envelope polypeptides having a structure that approximates conformational discontinuous epitopes of a primate lentivirus envelope protein, but as a result of modifications of glycosylation sites on that structure raises a greater range of antibodies to conserved epitopes, and/or has enhanced immunogenicity for broadly neutralizing epitopes.

BACKGROUND OF THE INVENTION

Human immunodeficiency virus type 1 (HIV-1) is the cause of acquired immunodeficiency syndrome (AIDS), which is characterized by the depletion of CD4-positive lymphocytes (1,2). Infection of humans by HIV-1 typically involves an initial period of acute, high-level viremia, followed by a chronic, low-level viremia (3–6). It is thought that the antiviral immune response helps to determine the "set-point" for chronic viremia. HIV-1 persistence results in progressive CD4-positive lymphocyte decline, which ultimately compromises the immune response, including that directed against HIV-1(6). The resulting resurgence of high-level viremia is a harbinger of poor clinical outcome (6,7).

The envelope protein of a lentivirus is the most visible portion of the virion because it is on the surface of the virus particle. Thus, considerable attention has focussed on the envelope protein as a target for inhibiting viral entry. Strategies that have been used include using the envelope protein to generate an immune response, decoys for the envelope protein, etc. These approaches have not yet been successful.

It was recently reported that a large scale clinical trial was going to be attempted with an HIV envelope protein as an immunogen. While the initial trials with the protein have not been reported to be promising in terms of showing any significant protective immunity, they have also not indicated any significant harm caused by the vaccine candidate. The fact that a clinical trial with this type of preliminary results would be attempted shows the importance placed upon the use of the envelope protein and the need for improvements in the envelope protein that can be used such as by selectively enhancing its immunogenicity.

HIV-1 is tropic for CD4-positive cells by virtue of the high affinity interaction between the HIV-1 exterior envelope glycoprotein, gp 120, and CD4, which acts as the primary virus receptor (1,2,3). The gp 120 molecule is derived by proteolytic cleavage from the precursor gp 160 glycoprotein and noncovalently associates with the transmembrane glycoprotein, gp41, to form trimeric complexes on the virus or cell surface (4,5,6,7). The gp 160 precursor is initially modified by the addition of high-mannose sugars at approximately 28 N-linked glycosylation sites of the approximately 845–870 amino acid primary translation product. A subset of the high-mannose sugars becomes modified to complex carbohydrates following oligomerization and cleavage of the gp 160 precursor in the Golgi apparatus.

The envelope protein is an attractive target because, like that of other retroviruses, the entry of HIV-1 into target cells is mediated by the viral envelope glycoproteins, gp 120 and gp41, which are derived from a gp 160 precursor (See, Allan, J S, et al., "Major Glycoprotein Antigens That Induce Antibodies in AIDS Patients are Encoded by HTLV-III," *Science* 228:1091–1093 (1985); Robey, W G., et al., "Characterization of Envelope and Core Structural Gene Products of HTLV-III with Sera from AIDS Patients," *Science* 228:593–595 (1985)). The gp 160 glycoprotein is created by the addition of N-linked, high mannose sugar chains to the approximately 845–870 amino acid primary translation product of the env gene in the rough endoplasmic reticulum. Trimerization of gp 160 in the endoplasmic reticulum is mediated by the formation of a coiled coil within the gp41 ectodomain. (See, Earl, P L., et al., "Oligomeric Structure of the Human Immunodeficiency Virus Type 1 Envelope Glycoprotein," *Proc. Natl. Acad. Sci. USA* 87:648–652 (1990); Pinter, A., et al., "Oligomeric Structure of gp41, the Transmembrane Protein of Human Immunodeficiency Virus Type 1, " *J. Virol.* 63:2674–2679; Lu, M., et al., "A Trimeric Structural Domain of the HIV-1 Transmembrane Glycoprotein," *Nature Structural Biol.* 2:1075–1082 (1995); Chan, D C, et al., "Core Structure of gp41 from the HIV Envelope Glycoprotein," *Cell* 89:263–273 (1997); and Weissenhorn, W., et al., "Atomic Structure of the Ectodomain from HIV-1 gp41," *Nature* 387:426–430 (1997)). The gp 160 trimers are transported to the Golgi apparatus, where cleavage by a cellular protease generates the mature gp 120 and gp41 glycoproteins, which remain associated through non-covalent interactions (Earl, P L, et al., "Folding, Interaction with GRP78-BiP, Assembly and Transport of the Human Immunodeficiency Virus Type 1 Envelope Protein," *J. Virol.* 65:2047–2055 (1991); and Kowalski, M., et al., "Functional Regions of the Envelope Glycoprotein of Human Immunodeficiency Virus Type 1," *Science* 237:1351–1355 (1987)). In mammalian host cells, addition of complex sugars to selected, probably surface-exposed, carbohydrate side chains of the envelope glycoproteins occurs in the Golgi apparatus. (See, Leonard, C K, et al., "Assignment of Intra chain Disulfide Bonds and Characterization of Potential glycosylation Sites of the Type 1 Recombinant Human Immunodeficiency Virus Envelope Glycoprotein (gp 120) Expressed in Chinese Hamster Ovary Cells," *J. Biol. Chem.* 265:10373–10382 (19990)).

Most of the surface-exposed elements of the oligomeric envelope glycoprotein complex are contained on the gp 120 exterior envelope glycoprotein. (See, Moore, J., et al., "Probing the Structure of the Human Immunodeficiency Virus Surface Glycoprotein gp 120 with a Panel of Monoclonal Antibodies," *J. Virol.* 68:469–484 (1994)). When the gp 120 glycoproteins derived from different primate immunodeficiency viruses are compared, five conserved regions (C1 to C5) and five variable regions (V1 to V5) can be identified. (See, Starcich, B R, et al., "Identification and Characterization of Conserved and Variable Regions of the Envelope Gene HTLV-III/LAV, the Retrovirus of AIDS,"

Cell 45:637–648 (1986); Myers, G., et al. "Human Retroviruses and AIDS: A Compilation and Analysis of Nucleic Acid and Amino Acid Sequences," Los Alamos National Laboratory, (1994)). Intramolecular disulfide bonds in the gp 120 glycoprotein result in the incorporation of the first four variable regions into large, loop-like structures. Antibody binding studies and deletion mutagenesis have indicated that the major variable loops are well-exposed on the surface of the gp 120 glycoprotein. (See, Wyatt, R., et al., "Functional and Immunologic Characterization of Human Immunodeficiency Virus Type 1 Envelope Glycoproteins Containing Deletions of the Major Variable Regions," J. Virol. 7:4557–4565 (1993); Pollard, S., et al., "Truncated Variants of gp 120 bind CD4 with High Affinity and Suggest a Minimum CD4 Binding Region," EMBO J. 11:585–591 (1992)).

The mature envelope glycoprotein complex is incorporated into HIV-1 virions, where it mediates virus entry into the host cell. The gp 120 exterior glycoprotein binds the CD4 glycoprotein, which serves as the primary receptor. (See, Klatzmann, D., et al., "T-lymphocyte T4 Molecule Behaves as the Receptor for Human Retrovirus LAV," Nature London 312:767–768 (1984); and Dalgleish, A G., et al., "The CD4 (T4) Antigen is an Essential Component of the Receptor for the AIDS Retrovirus," Nature 312:763–767 (1984)). The association of gp 120 with CD4 is mediated by the interaction of a discontinuous gp 120 structure with the CDR2-like region of the CD4 amino-terminal domain. (See, Brodsky, M H., et al., "Analysis of the Site in CD4 that Binds to the HIV Envelope Glycoprotein," J. Immunol. 144:3078–3086 (1990); Peterson, A., et al., "Genetic analysis of Monoclonal Antibody and HIV binding Sites on the Human Lymphocyte Antigen CD4," Cell 54:65–72 (1988); Moebius, U., et al., "The Human Immunodeficiency Virus gp 120 Binding Site on CD4: Delineation by quantitative Equilibrium and Kinetic Binding Studies of Mutants in Conjunction with a High-Resolution CD4 Atomic Structure," J. Exp. Med. 176:507–517 (1982); Arthos, J., et al., "Identification of the Residues in Human CD4 Critical for the binding of HIV," Cell 57:469 (1989); Ryu S E., et al., "Crystal Structure of an HIV-binding Recombinant Fragment of Human CD4," Nature London 348:419–425 (1990); and Wang, J., et al., "Atomic Structure, of a Fragment of Human CD4 containing Two immunoglobulin-like Domains," Nature London 348:411–418 (1990)). Amino acids in the gp 120 C3 and C4 regions have been implicated in CD4 binding. (See, Cordonnier, A., et al., "Single Amino Acid Changes in HIV Envelope Affect Viral Tropism and Receptor Binding, Nature 340:571–574 (1989); Lasky, L., et al., "Delineation of a Region of the Human Immunodeficiency Virus Type 1 gp 120 Glycoprotein Critical for Interaction with the CD4 Receptor," Cell 50:975–985 (1987); and Olshevsky, U., et al., "Identification of Individual HIV-1 gp 120 Amino Acids Important for CD4 Receptor Binding," J. Virol. 64:5701–5707 (1990)). The association of gp 120 with CD4 is believed to initiate conformational changes in the HIV-1 envelope glycoprotein complex, leading to interactions with members of the chemokine receptor family. (See, Sattentau, Q., et al., "Conformational Changes Induced in the Human Immunodeficiency Virus Envelope Glycoprotein by Soluble CD4 binding," J. Exp. Med. 174:407–415 (1991); Thali, M., et al., "Characterization of Conserved Human Immunodeficiency Virus Type 1 (HIV-1) gp 120 neutralization Epitopes Exposed Upon gp 120-CD4 Binding," J. Virol 67:3978–3988 (1993); Sattentau, Q., et al., "Conformational Changes Induced in the Envelope Glycoproteins of Human and Simian Immunodeficiency Virus by Soluble Receptor Binding," J. Virol. 67:7388–7393 (1993); Trkola, A., et al., "CD4-dependent, antibody-sensitive Interactions Between HIV-1 and its Co-receptor CCRO5," Nature 384:184–187 (1996); and WU, L., et al., "CD4-induced Interaction of Primary HIV-1 gp 120 Glycoproteins with the Chemokine Receptor CCR5," Nature 384:179–183 (1996).

Chemokine receptors are G protein-coupled, seven-membrane-spanning proteins involved in leukocyte chemotaxis. (See, Baggioline, M., et al., "Interleukin-8 and Related Chemotactic Cytokines-CXC and CC Chemokines," Adv. Immunol. 55:97–179 (1994); Gerard, N., et al., "the Pro-Inflammatory Seven-Transmembrane-Segment Receptors of the Leukocyte," Curr. Opin. Immunol. 6:140–145 (1994); and Premack, B A., et al, "Chemokine Receptors: Gateways to Inflammation and Infection," Nature Medicine 11:1174–1178 (1996)). Most laboratory-adapted HIV-1 viruses utilize a CXC chemokine receptor called CXCR4 (also called LESTR, HUMSTSR or fusin), while most macrophage-tropic primary HIV-1 viruses use the CC chemokine receptor CCR5 (see, Feng, Y., et al., Science 272:872–877 (1996); Choe, H., et al., Cell 85:1135–1148 (1996); Deng, H K., et al., Nature 381:661–666 (1996); Dragic, T., et al., Nature 381:667–673 (1996); Doranz, B J., et al., Cell 85:1149–1158 (1996); and Alkhatib, G., et al., Science 272:1955–1958 (1996)), and to an extent CCR3 or CCR2. Primary dual-tropic HIV-1 isolates use CCR5 as well as CXCR4. (See, Zhang, L., et al., Nature 383:768 (1996) and Connor, R., et al., J. Exp. Med. 185:21–628 (1997)). The macrophage-tropic primary viruses are those most often transmitted from infected to uninfected individuals, and predominate during the long, asymptomatic phase of infection. (See, Cheng-Mayer, C., et al., Science 240:80–82; Zhu, T., et al., Science 261:1179–1181 (1993); Fenyo, E., J. Virol. 62:4414–4419 (1988); Schuitemaker, H., et al., J. Virol. 66:1354–1360 (1991); and Connor, R I., et al., J. Virol. 67:1772–1778 (1993)). The importance of CCR5 for HIV-1 transmission is underscored by the observation that humans with homozygous defects in CCR5 are relatively resistant to HIV-1 infection. (See, Liu, R., et al., Cell 86:367–378 (1996); Samson, M., et al., Nature 10 382:722–725 (1996); and Dean M., et al., Science 273:1856–1862 (1996)). CCR5 is used as a corrector by almost all primary HIV-1 isolates regardless of geographic clade, and is used by the related human and primate immunodeficiency viruses, HIV-2 and simian immunodeficiency virus, SIV. (See, Marcon, L., et al., J. Virol 71:2522–2527 (1997); Chen, Z., et al., J Virol. 71:2705–2714 (1997); and Cocchi, F., et al., Science 270:1811–1815 (1995)). This suggests that at least part of the viral binding site for CCR5 is well-conserved among these immunodeficiency viruses. While these gp 120 structures are under investigation and have yet to be completely defined, mutagenic studies have suggested that elements of the V3 loop may constitute part of the chemokine receptor binding site. Genetic studies of viruses with chimeric HIV-1 envelope glycoproteins containing different V3 loops demonstrated that the gp 120 V3 region is a major determinant of which chemokine receptor, CCR5 or CXCR4, can be used as an,entry cofactor. (See, Cocchi, F., et al., Nature med., 2:1244–1247 (1996); and Speck, R., et al., J. Virol. (in press)). Thus, even in the relatively variable background of the V3 domain, there may exist conserved structural features that collaborate with other conserved gp 120 structures to create a high-affinity binding site for CCR5.

It is likely that the interaction of the gp 120-CD4 complex with the appropriate chemokine receptor promotes additional conformational changes in the envelope glycoprotein complex. By analogy with the influenza hemoglutinin, it has been suggested that the HIV-1 gp41 ectodomain undergoes major conformational changes during virus entry. (See, Carr, C M., et al., *Cell* 73:823–832 (1993); Chen, C H., et al., *J. Virol.* 69:3771–3777 (1995); Bullough, P., et al. *Nature* 371:37–43 (1994); and Weissenhorn, W., et al., *EMBO J* 15:1507–1514 (1996)). The proposed result of these changes is the insertion of the hydrophobic gp41 amino terminus (the "fusion peptide") into the membrane of the target cell. Mutagenic analysis and the recently determined crystal structures of HIV-1 gp41 ectodomain fragments are consistent with this model (see, Freed, E., et al., *Proc. Natl. Acad. Sci USA* 87:4650–4654 (1990)).

The exposed nature of the HIV-1 envelope glycoproteins on the surface of virions or infected cells renders them prime targets for the antiviral immune response. In fact, the only viral proteins accessible to neutralizing antibodies are the envelope glycoproteins. Neutralizing antibodies appear to be an important component of a protective immune response, in chimpanzees challenged with HIV-1 (see, Berman, P W., et al., *Nature* 345:622–625 (1990); Girard, et al., *Proc. Natl. Acad. Sci. USA* 88:542–546 (1991); Emini, et al., *Nature* 355:728–730 (1991); and Bruck, et al., *Vaccine* 12:1141–1148 (1994). That neutralizing antibodies generated during the course of HIV-1 infection do not provide permanent antiviral effect may in part be due to the generation of neutralization escape virus variants (see, Nara, et al., *J. Virol.* 64:3779–3791 (1990); Gegerfelt, et al., *Virology* 185:162–168 (1991); and Arendrup, et al., *J AIDS* 5:303–307 (1992)), and to the general decline in the host immune system associated with pathogenesis.

HIV-1 neutralizing antibodies are mostly directed against linear or discontinuous epitopes of the gp 120 exterior envelope glycoprotein. Rare examples of gp41-directed neutralizing antibodies have also been documented (see, Muster, et al., *J. Virol.* 67:6642–6647 (1993)). Neutralizing antibodies that arise early in infected humans and that are readily generated in animals by immunization are primarily directed against linear neutralizing determinants in the third variable (V3) loop of gp 120 glycoprotein (see, Matthews, et al., *Proc. Natl. Acad. Sci. USA* 83:9709–9713 (1986); and Javaherian, et al., *Science* 250:1590–1593 (1990)). These antibodies generally exhibit the ability to neutralize only a limited number of HIV-1 strains, although some subsets of anti-V3 antibodies recognize less variable elements of the region and therefore exhibit broader neutralizing activity (see, Ohno, et al., Proc. Natl. Acad. Sci. USA 88:10726–10729 (1991); Moore, et al.,*J. Virol.* 69:122–133 (1995); and Gorny, et al., *J. Virol.* 66:7538–7542 (1992)). Envelope glycoprotein variation within the linear V3 epitope and outside of the epitope can allow escape of viruses from neutralization by these antibodies (see, McKeating, et al.,*J. Virol.* 67:4932–4944 (1993)). The second variable (V2) region of the HIV-1 envelope glycoprotein has also been shown to be a target for strain-restricted neutralizing antibodies (see, Fung, et al., *J. Virol.* 66:848–856 (19921; Moore, et al., *J. Virol.* 67:6136–6151 (1993)). Most of the V2 epitopes consist of continuous but conformation-dependent determinants.

Later in the course of HIV-1 infection of humans, antibodies capable of neutralizing a wider range of HIV-1 isolates appear (see, Profy, et al., *J. Immunol.* 144:4641–4647 (1990); Berkower, et al., *J. Exp. Med.* 170: 1681–1695 (1989); Ho, et al., *J. Virol.* 489–493 (1991); Kang, et al., *Proc. natl. Acad. Sci. USA* 88:6171–6175 (1991); Steimer, et al., *Science* 254:105–108 ((1991); and Moore et al., *J. Virol.* 67:863–875 (1993)). These broadly-neutralizing antibodies have been difficult to elicit in animals (see, Rusche et al., *Proc. Natl. Acad. Sci. USA* 84:6924–6928 (1987); Klaniecki et al., *AIDS Res. Hun; Retro.* 7:791–798 (1991); and Haigwood, et al., *J. Virol.* 66:172–182 (1992)), and are not merely the result of additive anti-V3 loop reactivities against diverse HIV-1 isolates that accumulate during active infection. A subset of the broadly reactive antibodies, found in most HIV-1-infected individuals, interferes with the binding of gp 120 and CD4. At least some of these antibodies recognize discontinuous gp 120 epitopes (the so-called CD4BS epitopes) present only on the native glycoprotein. Human monoclonal antibodies derived from HIV-1-infected individuals have been identified that recognize the gp 120 glycoproteins from a diverse range of HIV-1 isolates, that block gp 120-CD4 binding, and that neutralize virus infection (see, Posner, et al., *J. Immunol.* 146:4325–4332 (1991); and Tilley, et al., *Res. Virol.* 142:247–259 (1991)). Some of these CD4BS-directed antibodies efficiently neutralize primary HIV-1 isolates (see, Burton, et al., *Science* 266:1024–1027 (1994)), which are generally more resistant to neutralization than are viruses passaged in immortalized cell lines (see, Daar, et al., *Proc. Natl. Acad. Sci. USA* 87:6574–6578 (1990); Wrin, et al., *J. virol.*69:39–48 (1995); Sullivan, et al., *J. Virol.* 69:4413–4422 (1995); Sawyer, et al.,*J. Virol.* 67:1342–1349 (1994); Moore, et al., *J. Virol.* 69:101–109 (1995); and D'Souza, et al., *J. Infect. Dis.* 175:(in press)(1997)). The discontinuous epitopes recognized by many of the human monoclonal antibodies directed against the CD4BS epitopes have been characterized by mutagenic analysis (see, Thali, et al., *J. Virol.* 65:6188–6193 (1991); Thali, et al., *J. Virol.* 66:5635–5641 (1992); McKeating, et al., Virology 190:134–142 (1992)). Amino acid changes in seven discontinuous gp 120 regions, four of which overlap regions defined to be important for CD4 binding, disrupt recognition by these antibodies and, in some cases, allow the generation of neutralization escape mutants.

A second group of neutralizing antibodies found in a smaller number of HIV-1-infected humans is directed against conserved gp 120 epitopes that are exposed better upon CD4 binding (see, Thali, et al.,*J. Virol.* 67:3978–3988 (1993)). These epitopes, referred to as the CD4-induced (CD4i) epitopes, are extremely sensitive to conformational changes in the gp 120 glycoprotein. The integrity of these epitopes is affected by gp 120 amino acid changes in the conserved stem of the V1/V2 stem-loop structure and in the C4 region. The CD4i epitopes have been shown to be proximal to the V3 loop and to be masked by the V1/V2 variable loops (see, Wyatt, et al., *J. Virol.* 69:5723–5733 (1995); and Moore, et al.,*J. Virol* 70:1863–1872 (1996)). It has been shown that CD4 binding induces a movement of the V1/V2 loops that exposes the CD4i epitopes. Interestingly, it has been shown that neutralizing antibodies directed against either the V3 loop or the CD4i epitopes block the ability of gp 120-CD4 complexes to bind CCR5. Thus, it appears that the major groups of neutralizing antibodies generated in HIV-1-infected humans block the binding of virus to its cellular receptors, either CD4 or the chemokine receptors.

The development of an HIV-1 vaccine as explained above has been hampered by the inefficiency with which antibodies directed against the more conserved gp 120 structures are elicited. Most of the antibodies elicited by the HIV-1 envelope glycoproteins, either in infected humans or chimps or in animals immunized with envelope glycoprotein preparations, are not able to neutralize virus. Many of these non-neutralizing antibodies are directed against gp 120 structures that are inaccessible on the native envelope glycoprotein complex due to interaction with the gp41 ectodomain (see, Wyatt, et al., (1997)). When neutralizing antibodies are elicited, these are often directed against variable portions of the HIV-1 envelope glycoproteins. Most of the neutralizing antibodies elicited by native HIV-1 gp 120 or gp 160 glycoproteins are directed against the V3 loop (see, Haigwood, et al., *AIDS Res. Hum. Retro.* 6:855–869 (1990)). Multiple immunizations with native gp 120 or gp 160 glycoproteins are required to elicit even low titers of neutralizing antibodies with broader strain reactivity. This same pattern of elicitation of neutralizing antibodies has been observed in HIV-1-infected humans or chimps, with antibodies directed against the V3 loop appearing earlier in infection. These results suggest that the structure of the HIV-1 gp 120 envelope glycoprotein has evolved to decrease the immunogenicity of particular epitopes in which variation is poorly tolerated by the virus. By the time immune responses to these epitopes are elicited, immune compromise has occurred, viral burden is high, and virus variation and the potential for neutralization escape has reached significant levels. These considerations suggest that use of the native, complete HIV-1 glycoprotein as an immunogen will most efficiently elicit the same types of immune responses that the virus has evolved to evade most efficiently. Improved immunogens based upon the envelope protein are necessary.

Previous studies have indicated that the relatively poor surface accessibility of the more conserved gp 120 epitopes related to the CD4 and chemokine receptor binding sites may in part provide an explanation for the low apparent immunogenicity of these regions (21). The V1/V2 and V3 variable loops of the HIV-1 gp 120 glycoprotein have been shown to mask the CD4BS epitopes, and removal of these variable regions results in a 5–50-fold increase in exposure of most of the CD4BS epitopes, on both the monomeric and the multimeric envelope glycoproteins (21). Removal of the V1 and V2 variable loops results in an increased exposure of HIV-1 gp 120 epitopes (V3 and CD4i epitopes) located near the binding site for the chemokine receptors. Thus, both of the receptor-binding regions of the HIV-1 gp 120 glycoprotein are partially masked by the large variable loop structures of the glycoprotein.

It is imperative that means of efficiently eliciting an array of antibodies directed against the more conserved gp 120 elements be developed.

SUMMARY OF THE INVENTION

We have now found polypeptides that are modified from a primate lentivirus such as the HIV-1 envelope glycoproteins that can raise a broader array of antibodies and/or have enhanced immunogenicity for its neutralization epitopes, particularly those such as the CD4bs and/or CD4i epitopes, than the wild-type gp 120 protein. The modifications include the selective deglycosylation of at least two carbohydrate addition sites proximal to the gp 120-CD4 binding site or chemokine receptor binding region. For example, in gp 120 of HIV-1, these would be sugar addition sites corresponding to amino acid residues 197, 276,301 and 386 using numbering based upon the HXBc2 strain. Corresponding sites in other strains and viruses can be selected by alignment of amino acid residues using standard computer programs in the default setting, or by aligning based upon using the receptor binding sites and then lining up the N-glycosylation sites.

In a second embodiment the sugars distal to the receptor binding sites can be derivatized with a molecular adjuvant such as C3d. These derivatized sugar molecules create a molecule that is more antigenic.

The modified gp 120 molecule containing the distally derivatized sugars can also have at least one of the sugar addition sites proximal to the receptor deglycosylated.

In a preferred embodiment, the gp 120 molecule has at least a portion of a variable region removed, preferably the V1/V2 loops, while retaining the conformation of a conserved conformational neutralization epitope of the wild-type gp 120 such as a CD4bs epitope.

Genetic modification of gp 120 or gp 120 variants to include a pan-reactive T cell helper epitope can improve the immunogenicity of weakly immunogenic conserved or glycosylated, variable gp 120 regions.

BRIEF DESCRIPTION OF THE FIGURES

FIG. 3A is a Ca tracing of the gp 120 core, which was crystallized in a ternary complex with two-domain sCD4 and the Fab fragment of the 17b antibody[12], is shown. The gp 120 core is seen from the perspective of CD4, and is oriented with the viral membrane at the top of the figure and the target cell. The inner gp 120 domain is colored red and the outer domain is colored yellow. The "bridging sheet" is colored orange. The N- and C-termini of the truncated gp 120 core are labeled, as are the positions of structures related to the gp 120 variable regions, V1–V5. The A, C, D and E surface loops[12] are shown. The position of the "Phe 43" cavity involved in CD4 binding is indicated by an asterisk. A gp 120 surface implicated in binding to the CCR5 chemokine receptor.

FIG. 3B is a view of the molecular surface of the gp 120 outer domain, from the perspective indicated in FIG. 3A.

The molecular surface in the figure on the left is colored according to the variability observed in gp 120 residues among primate immunodeficiency viruses. Red indicates residues conserved among all primate immunodeficiency viruses; orange, residues conserved in all HIV-1 isolates; yellow, residues exhibiting some variation among HIV-1 isolates; and green residues exhibiting significant variability among HIV-1 isolates membrane at the bottom. The position of the V5 region is shown. Also note the highly conserved glycosylation site (asparagine 356 and threonine/serine 358) within the HE loop, between the V5 and V4 regions. In the figure on the right, the V4 loop and the carbohydrates are modeled, as described in Materials and Methods. The complex carbohydrate addition sites used in mammalian cells[14] are colored light blue, and the high-mannose sites are colored dark blue. The gp 120 protein surface is shown in white. The variability of the gp 120 surface shown is underestimated since the V4 variable loop, which is not resolved in the structure, contributes to this surface (approximate location is indicated).

Figure 3A:
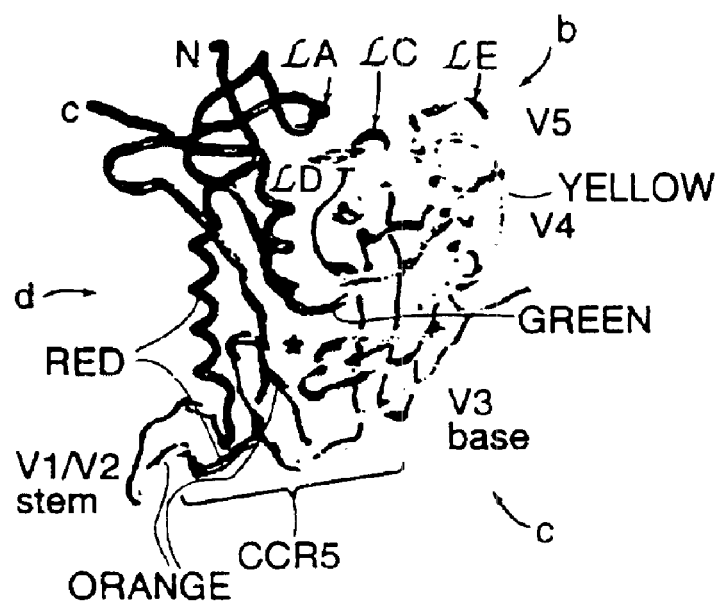
FIGS. 3A–3D show the structure and orientation of the HIV-1 gp 120 core.
Figure 3B:
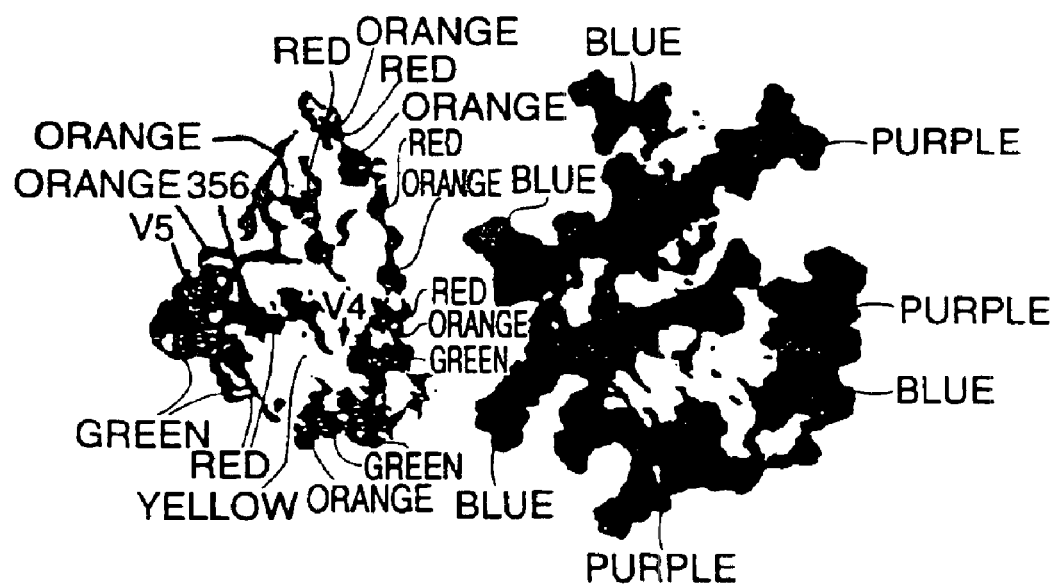
Figure 3C:
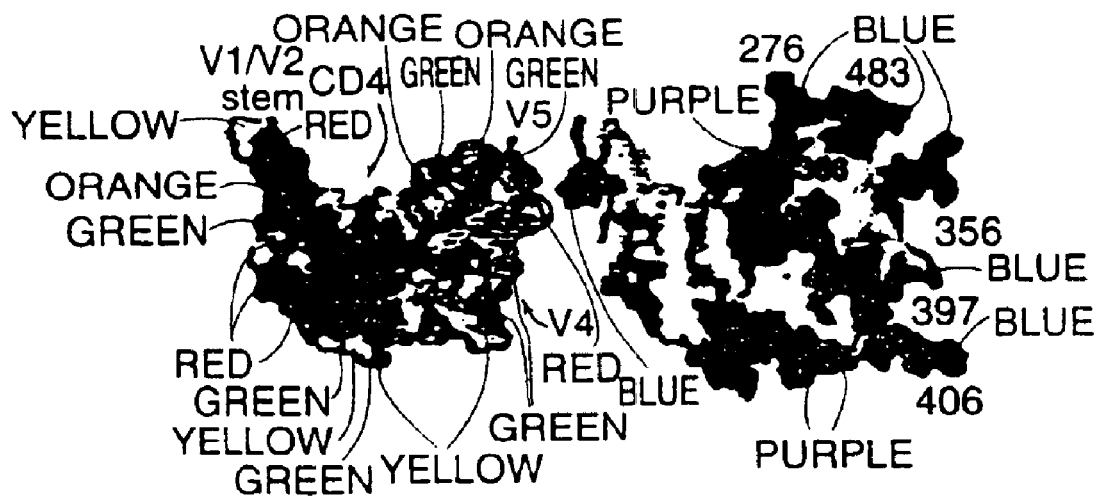

FIG. 3C is a view of the gp 120 molecular surface facing the target cell. Variability is indicated in the figure on the left, using the same coloring scheme as in 3B. Note the clear demarcation between the conserved surface, which has been implicated in the formation of CD4i epitopes[18] and in chemokine receptor binding (C. Rizuto and J. Sodroski, unpublished observations), and the variable surface of the outer domain. The recessed binding site for CD4 is indicated, flanked by the V1/V2 stem, which is labeled. The V4 loop and the carbohydrates are modeled in the figure on the right. The figure is colored as indicated in 3B. Particular carbohydrates referred to elsewhere are labeled.

Figure 3D:
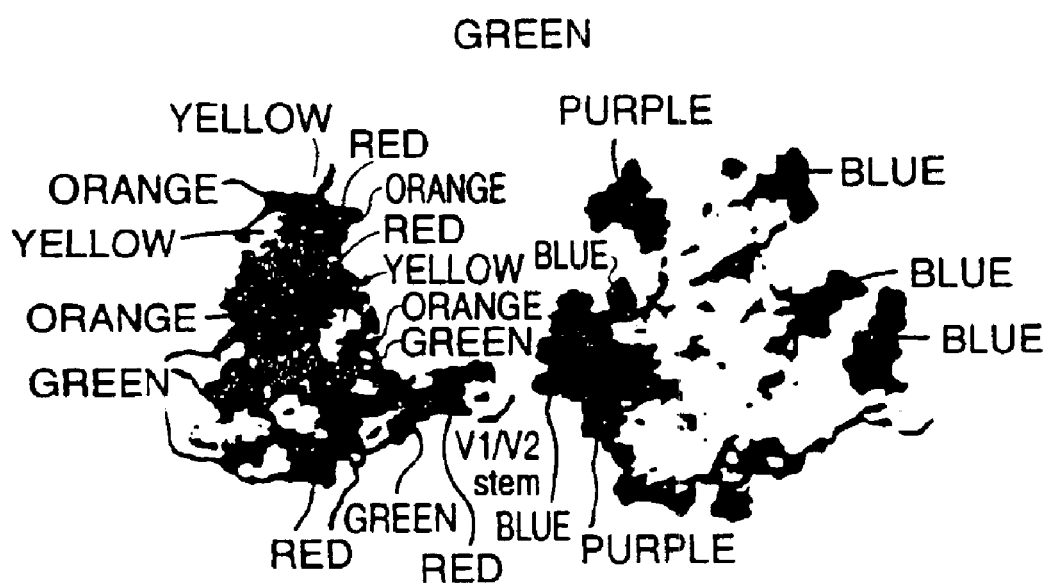

FIG. 3D is a view of the molecular surface of the gp 120 core inner domain. In the figure on the left, variability is indicated by the coloring scheme used in 3B. The CD4-binding site is to the right of the figure, and the protruding V1/V2 stem is indicated. The conserved molecular surface, which is associated with the inner domain of the gp 120 core, is devoid of known N-linked glycosylation sites. These are modeled in the figure on the right, which is colored as described in 3B.

FIGS. 4A–4D show the spatial relationship of epitopes on the HIV-1 gp 120 glycoprotein.

Figure 4A:
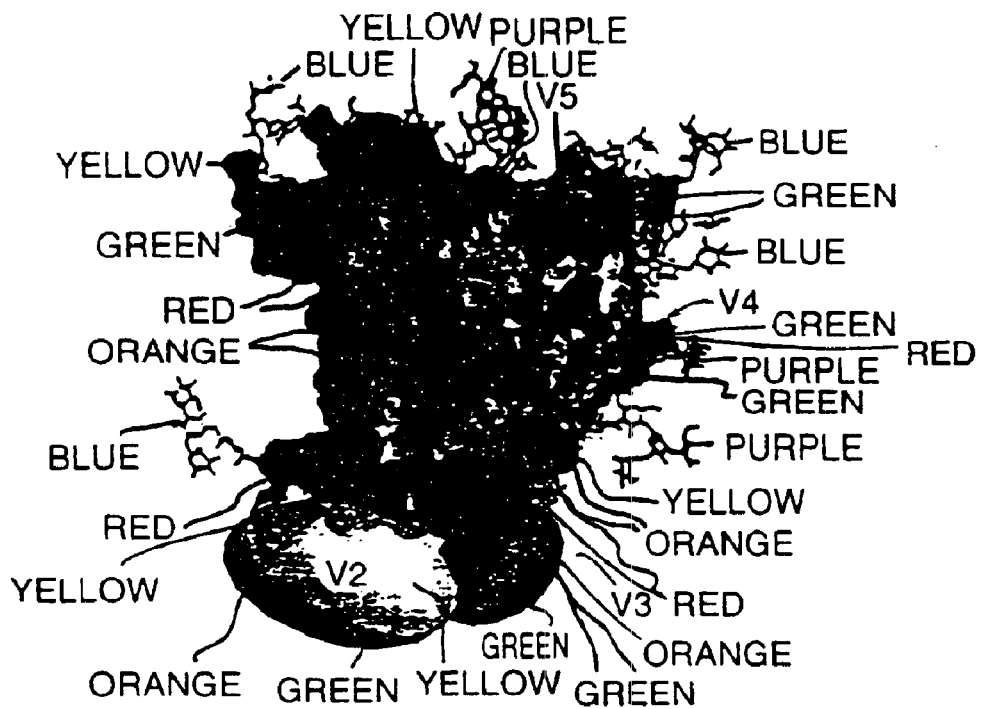

FIG. 4A shows the molecular surface of the gp 120 core from the same perspective as that in FIG. 3A. The modeled N-terminal gp 120 core residues, V4 loop and carbohydrate structures are included. The variability of the molecular surface is indicated, using the color scheme described in FIG. 3B. The modeled carbohydrates are colored light blue (complex sugars) or dark blue (high-mannose sugars). The approximate locations of the V2 and V3 variable loops are indicated. Note the well-conserved surfaces near the "Phe 43" cavity and the chemokine receptor-binding site (see FIG. 3A).

Figure 4B:
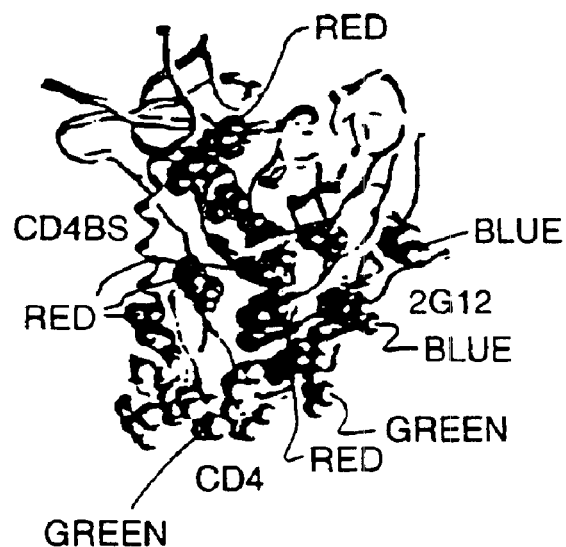

FIG. 4B is a Ca tracing of the gp 120 core, oriented similarly to FIG. 3A. The gp 120 residues within 4A of the 17b CD4i antibody are shown in green. The residues implicated in the binding of CD4BS antibodies20 are shown in red. Changes in these residues significantly affect the binding of at least 25 percent of the CD4BS antibodies listed in Table 1. The residues implicated in 2G12 bindings are shown in blue. The V4 variable loop, which contributes to the 2G12 epitope, '9 is indicated by dotted lines (see FIG. 3A).

Figure 4C:
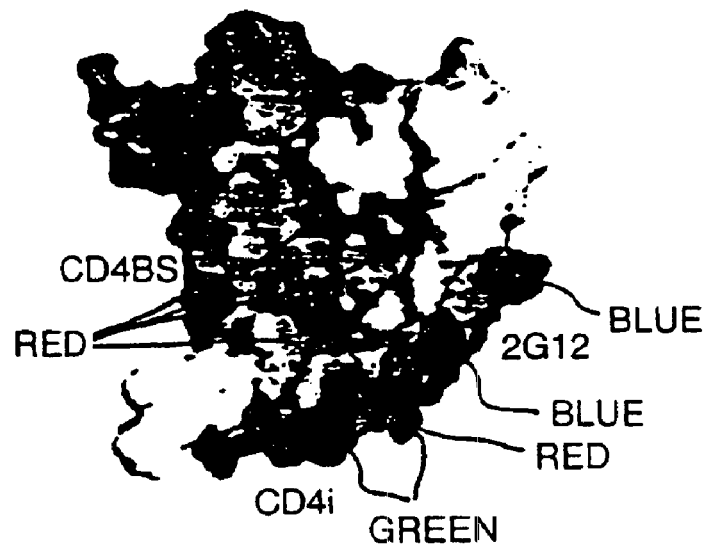

FIG. 4C is the molecular surface of the gp 120 core, oriented and colored as in 4B, is shown.

Figure 4D:
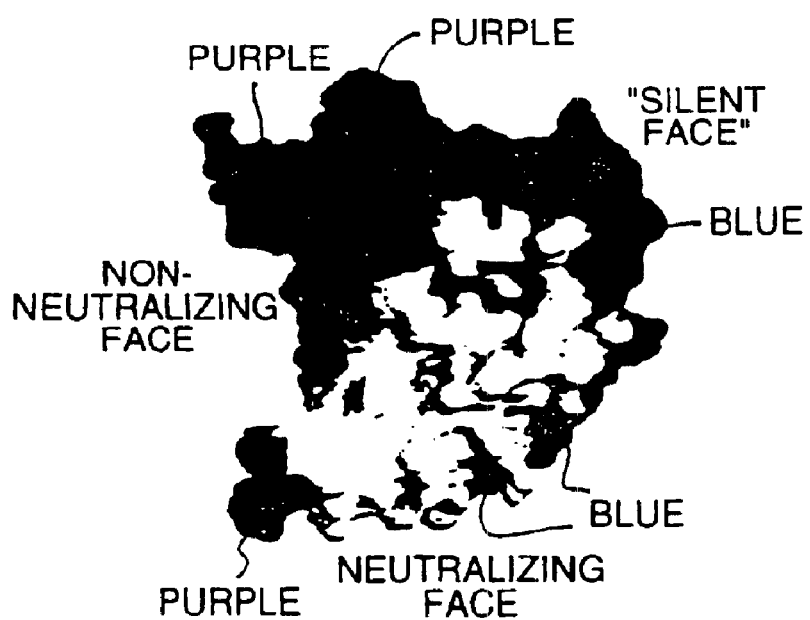

FIG. 4D shows the approximate locations of the faces of the gp 120 core, defined by the interaction of gp 120 and antibodies. The molecular surface accessible to neutralizing ligands (CD4 and CD4BS, CD4i and 2G12 antibodies) is shown in white. The neutralizing face of the complete gp 120 glycoprotein includes the V2 and V3 loops, which reside adjacent to the surface shown (see FIG. 4A). The approximate location of the gp 120 face that is poorly accessible on the assembled envelope glycoprotein trimer and therefore elicits only non-neutralizing antibodiesS6 is shown in purple. The approximate location of an immunologically “silent” face of gp 120, which roughly corresponds to the highly glycosylated outer domain surface, is shown in blue. Distance of each of the gp 120 monomers from the 3-fold symmetry axis is arbitrary.

FIG. 5 is a likely arrangement of the HIV-1 gp 120 glycoproteins in a trimeric complex. The gp 120 core was organized into a trimeric array, based on the criteria discussed in the text. The perspective is from the target cell membrane, similar to that shown in FIG. 3C. The CD4 binding pockets are indicated by black arrows, and the conserved chemokine receptor-binding regions are colored red. The areas shaded light green indicate the more variable, glycosylated surfaces of the gp 120 cores. The approximate locations of the 2G12 epitopes are indicated by blue arrows. The approximate locations for the V3 loops (yellow) and V4 regions (green) are shown. The positions of the V5 regions (green) and some complex carbohydrate addition sites (asparagines 276, 463, 356, 397 and 406) (blue dots) are shown. The approximate locations of the large V1/V2 loops, centered on the known positions of the V1/V2 stems, are indicated (green). On one of the gp 120 subunits, the positions of the ID and HE loops are indicated.

DETAILED DESCRIPTION OF THE INVENTION

It is important to elicit humoral immune responses directed toward conserved, functional elements of the HIV-1 exterior envelope glycoprotein, gp 120. Two functions common to virtually all primate lentiviruses such as the HIV-1 exterior envelope glycoproteins are the ability to bind the primary virus receptor, CD4, and to bind the more recently defined co-receptors. The co-receptors belong to a particular subset of the chemokine receptor family. The present polypeptides unmask the recessed CD4 binding site of gp 120 or better expose the putative chemokine receptor binding region by targeted deglycosylation. In an alternative approach, the remaining carbohydrate moieties are used to orient the CD4 binding site for more efficient presentation to the humoral immune system. These immunogens should elicit a greater percent of the more broadly neutralizing antibodies, as compared with the wild-type envelope glycoproteins such as gp 120.

The selective deglycosylation of at least two of four specific carbohydrate addition sites proximal to the gp 120-CD4 binding site or chemokine receptor binding region will better expose these regions, allow native gp 120 conformation to be maintained, and better elicit antibodies directed against these conserved envelope glycoprotein structures. Preferably, this deglycosylation is used with HIV-1 or HIV-2 envelope proteins, more preferably HIV-1. For example, with HIVgp 120 the sites are at amino acid residues 197, 276, 301 and 386, using the numbering of HXBc2 as a reference. The corresponding sites can readily be determined by aligning the CD4 binding site or the chemokine binding region and then looking for the proximal N-glycosylation sites. This can also be done by using BLAST 2.0 such as BLAST 2.0.4 and 2.0.5 available from the NIH (See www.ncbi.nlm.nkh.gov/BLAST/newblast.html) (Altschul, S. F., et al. Nucleic Acids Res. 25: 3389–3402 (1997))and DNASIS (Hitachi Software Engineering America, Ltd.).

In an alternative embodiment, biochemically derivatizing the sugars located distal to receptor binding sites with an orienting molecule such as recombinant C3d-cysteine utilizing periodate oxidation and a heterobifunctional cross-linker permits a greater control of orientation of the molecule during the process of antigen presentation. These gp 120-C3d complexes will better expose neutralizing determinants to the humoral immune system, presumably by targeted orientation of such complexes, in a C3d-dependent manner, to complement receptors (CD21) located on the surface of antigen presenting cells (APCs).

During the course of HIV-1 infection, neutralizing antibodies are elicited against various elements of gp 120 (15,16). Neutralizing antibodies appear to be an important component of the host immune response. In several animal models, the level of circulating neutralizing antibodies correlate with protection against virus challenge (17,18). Most clinical (primary) HIV-1 isolates are relatively resistant to neutralizing antibodies, suggesting that these viruses are actually selected for by the presence of neutralizing antibodies in infected humans.

In many HIV-1 infected individuals, two classes of neutralizing antibodies are elicited: strain-restricted and broadly cross-reactive antibodies. The strain-restricted antibodies appear early after infection and are generally directed against linear determinants within the gp 120 third variable region or V3 loop. This class of antibodies has been relatively easy to generate in both primate and non-primate animal systems (19, 20). The second class of antibodies appears later following infection, but exhibits neutralizing ability extending to a broad range of HIV-1 isolates (21). A subset of the broadly-neutralizing antibodies recognize conformationally-dependent, discontinuous epitopes that overlap with the discontinuous CD4 binding site on gp 120 and are termed CD4 binding site antibodies (CD4bs). These antibodies appear to neutralize HIV-1 infection by interfering with gp 120-CD4 interaction (22–25). A second limited subset of broadly-neutralizing antibodies recognize discontinuous gp 120 epitopes that are better exposed upon CD4 binding and thus are referred to as CD4-induced (CD4i) antibodies (26,27). Both the V3 loop-directed antibodies and the CD4i antibodies appear to neutralize virus entry by blocking gp 120-chemokine receptor interaction. Presumably, the epitopes of both these antibody types partially overlap with gp 120 moieties involved in chemokine receptor binding. In naive individuals, the presence of broadly cross-reactive neutralizing antibodies and strain-restricted antibodies might help prevent or limit HIV-1 infection following exposure to the virus.

The broadly neutralizing antibodies, however, have been difficult to elicit in animals using wild-type gp 120 as an immunogen. As a chronic pathogen, HIV-1 apparently evolved many mechanisms to impede or delay the elicitation of broadly-neutralizing antibodies directed against conserved, conformationally-sensitive epitopes on the gp 120 glycoprotein. The masking of conserved structures by carbohydrate is one strategy HIV-1 appears to employ to subvert immune recognition by the humoral immune system.

Accordingly, the present polypeptides which maintains the conformation of the wild-type envelope protein with respect to the CD4bs and CD4i inducing epitopes, but wherein specific sugar sites have been selectively removed, i.e., those sites that appear to mask conserved envelope receptor binding regions, should generate a greater percentage of immune responses to the desired sites. These carbohydrate modified peptides will influence the exposure and presentation of these structures to the immune system and thereby enhance the elicitation of antibodies with an expanded breadth of neutralization capacity.

We have recently solved the crystal structure of a gp 120 core protein. We utilized an approach termed variational crystallography that, coupled with ligand stabilization, allowed us to achieve well-ordered crystals. Crystallography, which employs modification of flexible surface moieties, enhances the crystallization process by increasing the surface available for lattice contacts. To produce diffractable crystals, we found it necessary to delete the V1, V2 and V3 loops and short stretches at the N- and C-termini to generate the )C1)V1/2/3)C5 glycoprotein. This )C1)V1/2/3)C5 protein was produced in Drosophila cells, in which all the N-linked sugars remain as unmodified high-mannose residues. This is in contrast to gp 120 produced in mammalian cells, in which a subset of the more exposed sugar residues becomes modified to complex carbohydrate. Following purification, the )C1)V1/2/3)C5 glycoprotein was mostly deglycosylated by a combination of endoglycosidases. The deglycosylation procedure retains intact the N-acetylglucosamine residue most proximal to the asparagine residue to which it is linked, allowing us to position the location of most gp 120 sugar linkages retained in the current structure.

In the available crystal, the gp 120 protein is complexed with two highly relevant ligands, two-domain CD4 (D1D2) and the Fab fragment of a CD4i neutralizing antibody, 17b. The structure of the gp 120 core, including the CD4 binding site, is well-defined in the ternary complex. Analysis of the gp 120 secondary structure reveals a two-domain structure comprised of an inner and outer domain. The gp 120 CD4 binding site spans the interface between the two domains of gp 120. The CD4 binding site is characterized by its recessed nature located between two protruding, glycosylated surfaces (see FIGS. 1 and 2). Phenylalanine 43 from the first domain of CD4 protrudes into the opening of a deep cavity, making contacts with gp 120 residues W427 and E370; nearby, R59 from CD4 is salt-bridged to gp 120 D368. Many of the CD4-binding site antibodies isolated from infected individuals are sensitive to changes in these same W427, D368 and E370 residues, indicating that antibody access to the recessed CD4 binding site is achievable. However this region is most likely shielded from the immune system by several barriers, especially in the context of functional oligomers on the surface of the virus.

Figure 1:
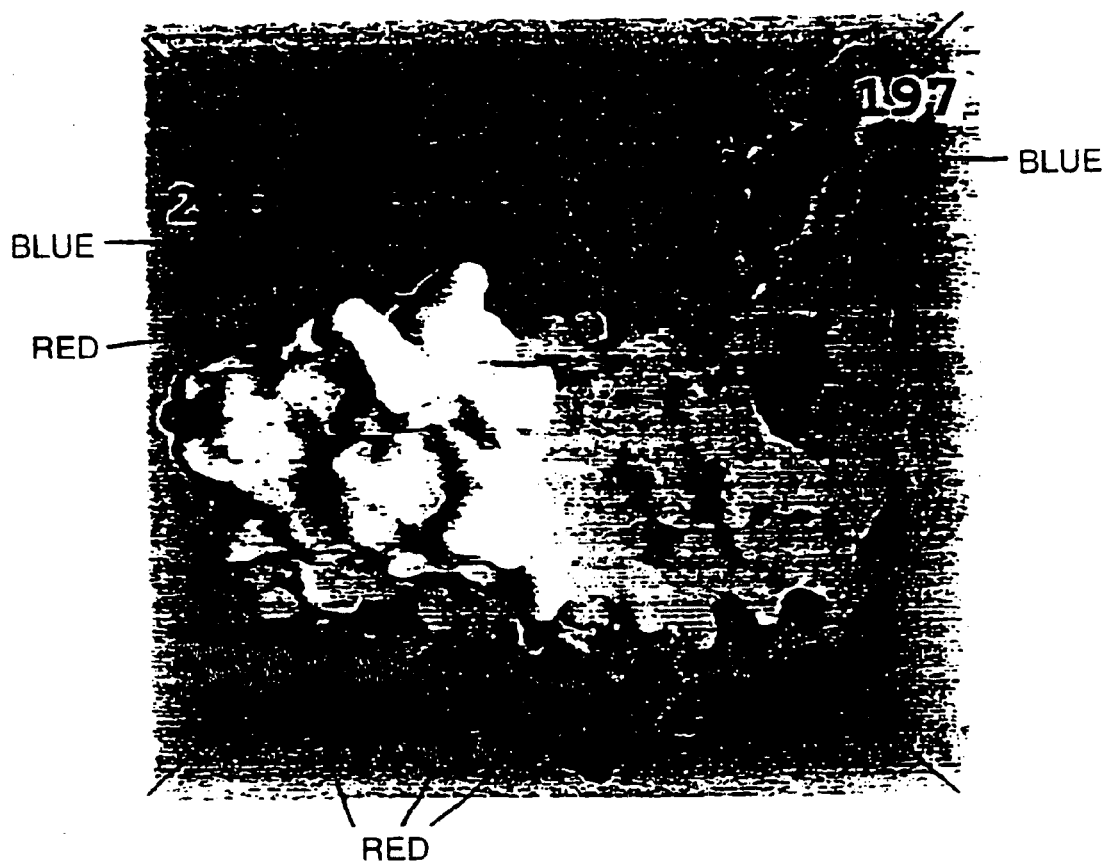
FIG. 1 shows the molecular surface of gp 120 viewed from the perspective of the viral membrane. In this orientation the N- and C-termini are facing the viewer (i.e. projecting out from the plane of the page). In the assembled oligomer, the N-and C-termini are most likely occluded by contacts with gp41 or by association with other gp 120 monomers. The V1/V2 stem projects toward the top of the page and contains residue N197 (labeled). A second protruding surface, adjacent to the recessed CD4 binding site (labeled and marked with an arrow), contains the N276 glycosylation site. The surfaces of the N-acetylglucosamnine residues at positions 197 and 276 are shaded in blue; other N-acetylglucosamine residues resolved in the structure and visible in this orientation are shaded in red. Note that the area occupied by the additional 6 or more sugar residues normally present in each N-linked carbohydrate (not shown) would cover a significant portion of the gp 120 surface.
Figure 2:
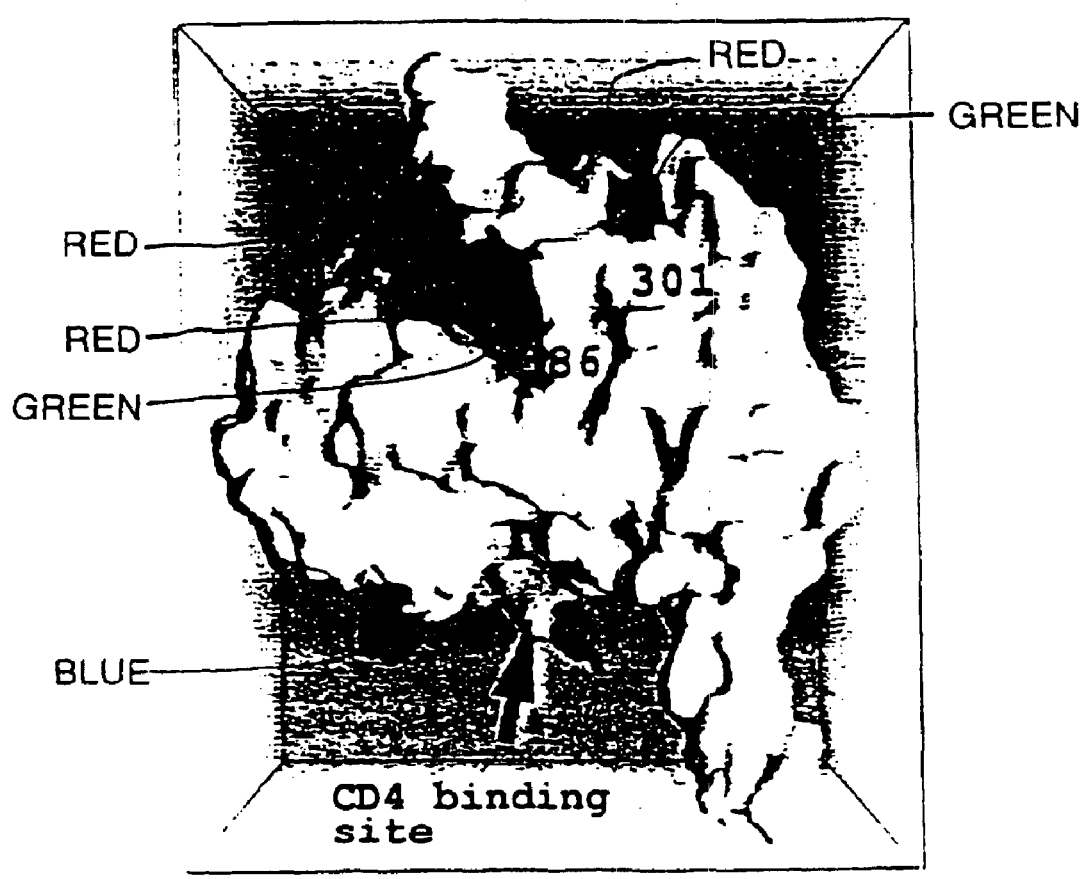
FIG. 2 shows the molecular surface of gp 120 viewed from the perspective of the target cell. As compared to the orientation in FIG. 1, gp 120 is rotated 180° on an X-axis projecting through the center of gp 120. The protruding V1/2 stem projects toward the bottom of the page and the putative chemokine receptor binding site is proximal to the N-acetylglucosamine residues (shaded in green) attached to the asparagines at 301 and 386 (labeled). The position of the N301 is approximate since in the available crystal most of the V3 loop is deleted and the stem of V3 extends only to residue 299. The orientation of the V3 stem and the requirement of the V3 loop for chemokine receptor binding suggests the intact V3 loop is likely to be proximal to the exposed surface circumscribed by N386, N301 and the base of the V1/V2 stem.

A B-cell or antibody must first penetrate the extensive glycosylation present on the oligomer surface. Access to the CD4 binding region is likely to be further restricted by the variable loops, especially the V1/V2 loops. Although these loops are not present in the current structure, the position of the V1/V2 stem remaining in the current structure lies in close proximity to D1D2 CD4 and to the CD4 binding site (FIGS. 1 and 2). This location is consistent with our previous demonstrations that, a) removal of the V1/2/3 variable loops increases recognition of gp 120 by CD4 binding site antibodies and b) removal of the V1/V2 loops eliminates the requirement for CD4 to induce maximally the 17b epitope (26, 28). The location of V1/V2 loops is thus proximal to the CD4 binding site. It is possible that, on the assembled oligomer, variable loops from adjacent monomers may influence access to CD4 binding sites on another subunit. This may be especially so on primary isolates, which are demonstrably more resistant to neutralizing antibodies than laboratory-adapted isolates (29). Finally, the recessed nature of the CD4 binding site pocket itself potentially contributes to impeding the access of antibodies to this region (see FIGS. 1 and 2). The structural constraints placed upon antibodies to circumvent the physical barriers impeding access to receptor binding regions apparently also contribute to the difficulty in eliciting these types of antibodies.

The present polypeptides eliminate two sugars that lie proximal to the CD4 binding site in the corresponding wild-type envelope protein. These sugars are located on either rim of the CD4 binding pocket on gp 120 (N197 and N276; FIG. 1).

The numbering is based upon the HXBc2 numbering and the analogous amino acid residues can readily be determined by the skilled artisan by known means. For example, alignment of strains using a standard amino acid homology program under default conditions as discussed above, or by lining up the CD4 binding sites and aligning the flanking amino acids based upon that alignment. The targeted deglycosylation polypeptides can be made based upon the whole polypeptide or using polypeptides, where at least a portion of a variable region has been removed. For example, one where the V1/V2 loops has been removed while inserting a linker residue to maintain the overall conformation of the desired epitope, e.g., the CD4bs and/or CD4i region, when an antibody to the CCR receptor is desired, the portion of the V3 region responsible for CCR binding is preferably retained. We expect that the V1/V2 loop removal will further enhance receptor binding site exposure. If better exposure of the CD4 binding site is the goal for a given immunogen, an envelope glycoprotein from a laboratory-adapted virus might be preferable, since the CD4 binding site may already exhibit somewhat greater exposure. To elicit a neutralizing response of greater breadth, a combination (cocktail) of optimized immunogens, derived from several envelope glycoproteins, will be of benefit to elicit antibodies directed against shared, conserved epitopes.

Prime/boosting with a mixture of immunogens or sequential immunization of distinct immunogens can be used as desired to elicit antibodies against structural elements shared in common among the selected gp 120 immunogens.

If the chemokine receptor-binding site, which presumably includes a portion of the V3 loop, is the immunogenic target, then a primary envelope derived from an R5 virus, such as JR-FL, is preferable.

Mutations of two additional sugar sites may better expose the conserved elements of the CCR5 binding site. One of these sites is at the base of the V3 loop (N301) and the second is located in the C3 region of gp 120 (N386). Both are positioned to impede immune access to the putative chemokine receptor-binding site (FIG. 2). It appears that the chemokine receptor binding site is located in a region overlapping with portions of the 17b epitope and the V3 loop, based upon the ability of antibodies to both these sites to inhibit gp 120-chemokine receptor interaction (14, 30). Extensive mutagenic analysis we have carried out strongly suggests that a conserved gp 120 structure that exhibits partial overlap with the 17b epitope is involved in chemokine receptor binding (31).

Previous studies have been conducted to indluence gp 120 immunogenicity by enzymatic deglycosylation or by mutagenesis of selected sugar attachment sites (32–35). Most of these studies showed that, while antibody responses were selectively increased to the modified immunogen, responses to the wild-type envelope glycoprotein were not increased, or in some cases, diminished. Thus, generic deglycosylation or removal of sugars from sites unrelated to neutralization epitopes is unlikely to be of benefit. Previous studies have deleted individually each of the sugar addition sites focused on in this proposal, with negligible to more severe effects (N 197) on envelope structure (36). We believe that by deleting at least two of these sites and more preferably at least three of these sites, the prior problems are overcome. Indeed, it is even more preferable that all four of the designated sites are deleted.

In an alternative approach that could be used by itself or in combination with the selectively deglycosylated polypeptides, the polypeptide can be oriented to provide better exposure for antibody generation.

One difficulty in efficiently raising broadly neutralizing antibodies against conserved epitopes is that the gp 120 is bound on the surface of the follicular dendritic cells (FDCs) in a non-random orientation. The FDCs are resident antigen-presenting cells (APCs) in the germinal centers of the lymph node and express many proteins, including complement receptors, on their cell-surface. Some of the displayed proteins are likely targeted to complement receptors (CD21) following the proteolytic activation of complement C3d, which becomes covalently linked to foreign proteins via a reactive internal thiol. Little is known regarding the orientation of proteins or virions on the surface of these cells and it is likely that gp 120 is bound in a manner in which particular (non-neutralizing) epitopes are preferentially displayed, thus skewing the immune response in favor of these epitopes. The vast majority of the carbohydrate residues are located on the gp 120 surface opposite to the CD4 binding site. By biochemically derivatizing these sugars with e.g., a molecular adjuvant such as recombinant C3d molecules, CTLA4 or $F_c$ molecules, we can position the gp 120 CD4 binding site in an orientation exposed to the humoral immune system on the surface of CD2 1-positive APCs or B-cells.

A previous study has exploited the ability of C3d to target proteins to complement receptors on B-cells or APCs by covalent linkage of C3d multimers to a model protein, hen eggwhite lysozyme (MEL) (37). When three murine C3d subunits were appended to HEL (HEL-C3d3), the amount of antigen required for HEL-specific antibody production in mice could be decreased 10,000-fold. The use of C3d as a "molecular adjuvant" thus provides an attractive means of eliciting a vigorous antibody response and the specificity of C3d for CD21 allows directed targeting of C3d-linked proteins to particular cell-types. We have shown the ability of C3d to enhance gp 120 immunogenicity by genetically appending repeats of murine C3d moieties to the gp 120 N- or C-termini and generating recombinant gp 120-C3d fusion proteins. The C3d does enhance ELISA titers to gp 120 Preferably, following deletion of gp 120 sugars proximal to the receptor binding region, we plan to oxidize the receptor-distal sugars. The aldehydes generated by this oxidation process will be used to link gp 120, via a heterobifunctional cross-linker, to a recombinant C3d molecule that has been specifically engineered to contain a free C-terminal cysteine residue to facilitate this process. One use of C3d would be for the targeting function of C3d to CD21-positive APCs. Inherent in this C3d derivitization process is the potential to orient gp 120 receptor binding regions on the surface of APCs for better exposure to the humoral immune system. Since B-cells also express CD21, the molecular adjuvant properties of C3d may provide an additional quantitative enhancement of gp 120-directed antibody responses. This biochemical approach to utilize the binding specificity of C3d would complement but not overlap with its adjuvant properties discussed previously.

These polypeptides can be used with envelope polypeptides where the hydrophobicity of the cavities has been increased, disulfide bonds have been introduced, hydrophobicity across the domain interface has selectively been increased and/or Pro introduced at specific turns (see Sodroski et al., U.S. provisional application no. 60/089,580, filed Jun. 17, 1998). These complementary approaches of optimizing both the immunogen are expected to elicit a broader HIV-1 neutralizing response than currently obtained.

Besides being required for protein folding, the extensive level of gp 120 glycosylation may influence gp 120 interaction with the host immune system. Much of the glycosylated surface may be seen as "self" epitopes by the humoral immune system and be rendered immunologically "silent". The sugars may disrupt potential T cell helper or cytotoxic T-cell epitopes. By genetically engineering a pan-reactive T-cell helper epitope into another region of the gp 120 glycoprotein, it should be possible to utilize the immunological potential of the gp 120 silent face. (see, Dalum, et al., *Mol. Immunol.* 34:1113–1120 (1997); and Dalum, et al., *J. Immunol.* 157:4796–4804 (1996). Genetically modifying gp 120 or gp 120 variants to include a pan-reactive T cell helper epitope may improve the immunogenicity. Consequently, the glycosylation may impede access of immunoglobulins to conserved, functional regions.

At least two of four gp 120 glycosylation sites in the polypeptides of the present invention are mutated to eliminate the attachment of N-linked sugars to the asparagine residues at positions 197, 276, 301 and 386 (based upon HXBc2 residue numbers). Preferably both positions 197 and 276, as well as an additional residue, are changed. One can use a lab strain such as HxBc2 to enhance CD4 site directed antibody generation or an M-class strain such as JR-FL when focusing on a CCR site directed antibody.

Either the asparagine linkage residue itself can be directly mutated or alternatively the S/T residue of the NXS/T N-linked glycosylation consensus can be altered to eliminate glycosylation at a specific site. For example, the N-linked glycosylation recognition site at 276 can be eliminated by a T/L change at residue 278, since this change is tolerated in the envelope glycoprotein of the ANT70 strain (38). Mutations can be introduced by the Quick Change Protocol (Stratagene) directly into double-stranded plasmid DNA-encoding e.g., HXBc2 and JR-FL envelope glycoproteins with and without V1/V2 loop sequences.

The mutations can be made in the inducible Drosophila expression vector (pMt120). Each of the carbohydrate addition sites targeted is known to be used in Drosophila cells (Peter Kwong, personal communication). Following confirmation that esch mutation was successfully introouduced, as determined by restriction site analysis and sequencing, stable *Drosophila* S2 lines can be established for each mutant glycoprotein. Recombinant glycoproteins can be produced by heavy metal induction of the metallothionein promoter that is integrated into the genome of the S2 cells and controls envelope glycoprotein expression. Each glycoprotein can be purified by affinity chromatography as previously described (14).

In parallel to the establishment of stable S2 producer lines, envelope glycoprotein sequences, each harboring the confirmed glycosylation site mutations, can be subcloned into a mammalian expression vector, such as psl/Illenv (39). The mutant glycoproteins will transiently be expressed from this vector in 293T cells as soluble gp 120 molecules and metabolically labeled with 35S-cysteine and methionine. Confirmation of the structural integrity of the mutant glycoproteins can be determined by immunoprecipitation with conformationally-sensitive antibodies and recognition by sCD4. Antibodies directed against the CD4 binding site and those overlapping the putative chemokine receptor site can be included in this analysis to determine if deglycosylation increases exposure of these antibody epitopes as compared to wild-type glycoproteins. The mutants such as the JR-FL derived polypeptides can be assessed for their ability to bind to stable lines expressing CCR5, as described, for example, in reference 33.

The purified glycoproteins can be immunized into groups of mice in the non-denaturing Ribi adjuvant (Sigma). We have previously used Ribi adjuvant to elicit HIV-1 neutralizing antibodies in mice immunized with gp 120 glycoproteins (data not shown). Groups of mice immunized with a mixture of polypeptides, e.g., those derived from HXBc2 and JR-FL mutant glycoproteins, either in combination or by sequential inoculations can be used. Following several inoculations with wild-type and mutant glycoproteins, antisera from the mice can be tested for the presence of gp 120-specific antibodies by ELISA and immunoprecipitation. Once significant levels of gp 120-directed are detectable, the antisera can be tested or the presence of neutralizing antibodies.

The neutralizing capacity of antisera can be quantitated by utilizing an assay which will detect single round of HIV-1 entry. Recombinant HIV-1 lacking env and possessing a CAT reporter gene are complemented in trans with various envelope glycoproteins, allowing infection of CD4-positive T-cells. This assay can be used to determine the titer of homologous neutralization as well as the breadth of the neutralizing response by assessing the capacity of the antisera to cross-neutralize viruses with heterologous laboratory-adapted and primary envelope glycoproteins.

These selectively deglycosylated polypeptides should elicit antibodies capable of neutralizing a broad range of laboratory-adapted strains better than wild-type glycoproteins. In generating an immune response, the presence of such a rage of antibodies will have a valuable role by significantly diminishing the acute viremia phase observed in most individuals soon after infection with HIV-1. Those glycoproteins containing multiple glycosylation site mutations as opposed to the wild-type are preferred.

To derivatize the sugars distal from gp 120 receptor binding regions; gp 120 sugar residues containing vicinal hydroxyls will be oxidized to aldehydes using sodium meta-periodate ($NalO_4^-$, Reaction 1). These aldehydes can then be reacted with the hydrazide group on the heterobifunctional cross-linker MPBH (Pierce) to form hydrazones (Reaction 2).

The MBPH also contains a reactive melamide group, which is selective for sulfhydryls when the pH of the mixture is kept between 6.5 and 7.5 (Reaction 3). In *Drosophila* cells, we will produce recombinant murine C3d that has been genetically altered to remove its reactive group

1. The oxidation of a cis-diol to an aldehyde

$$R-CH(OH)-CH_2-OH \xrightarrow{NaIO_4^-} R-CHO$$

2. The reaction of an aldehyde with MPBH

Maleimide-Ph-$CH_2-CH_2-CH_2-C(=O)-N(H)-NH_2 \cdot HCl$ + $R-CHO$ →

Maleimide-Ph-$CH_2-CH_2-CH_2-C(=O)-N(H)-N=CH-R$ $P-SH$ + Maleimide-$R$ $\xrightarrow{per\ OS-FS}$ $P-S-$(succinimide)$-R$ Maleimide-$R$ $\xrightarrow{OH^+}$ $HO-C(=O)-CH=CH-C(=O)-N(H)-A$ $R = $ Ph-$CH_2-CH_2-CH_2-C(=O)-N(H)-NH_2 \cdot HCl$ In the left panel, Reaction 1 depicts the oxidation of vicinal (cis) hydroxyls of sugar residues to an aldehyde. Reaction 2 diagrams the reaction of the MBPH hydrazide group with the aldehyde. In the right panel, the third reaction of the MBPH maleimide group with the free sulfhydryl of a protein (i.e. C3dGGGC) is shown (Pierce).

Internal thiol. The altered C3d will be engineered to possess an N-terminal His$_6$-tag for purification, a thrombin cleavage site to remove the His tag following purification, and a C-terminal G-G-G-C (C3d-GGGC) tail to provide a readily accessible free sulfhydryl. The C3d-GGGC will then be reacted with the MBPH-gp 120 to form a stable thioester linkage between the maleimide group and the reactive sulfhydryl. This reaction was successfully used when conjugating soluble CD4 to thiol-containing proteins such as B-galactosidase or hemoglobin (41). Since there are several potentially reactive carbohydrates and several sugar residues within each carbohydrate moiety, even relatively inefficient reactions will extensively derivative gp 120 and selected gp 120 mutants with C3d.

Following dialysis/microconcentration, as described by the manufacturer, the gp 120 portion of a conjugate can be tested for structural integrity by conformationally-sensitive antibodies and by CD4 binding. The C3d function can be assessed by the ability of a conjugate to bind to CD21-positive cell lines, such as Raji cells, compared to the binding of unconjugated gp 120 to these cells. Once the structural integrity of each gp 120-C3dGGGC conjugate is confirmed, groups of mice can be inoculated and the antibodies elicited by a particular conjugate can be tested for antigen specificity and neutralizing capacity as described in the first specific aim.

The polypeptides of this invention can be used to generate a range of antibodies to gp 120. For example, antibodies that affect the interaction with the binding site can be directly screened for example using a direct binding assay. For example, one can label, e.g. radioactive or fluorescent, a gp 120 protein or derivative and add soluble CD4. There are various soluble CD4s known in the art including a two-domain (D1D2 sCD4) and a four-domain version. The labeled gp 120, or derivative, e.g., a conformationally intact deletion mutant such as one lacking portions of the variable loops (e.g. V1/V2) and in some instances constant regions and soluble CD4 can be added to medium containing a cell line expressing a chemokine receptor that the antibody will block binding to. In this example, the derivative will block binding to CCR5. Alternatively, when using a derivative from a T cell tropic gp 120 one would use a cell line that expresses CXCR4. Binding can then be directly measured. The antibody of interest can be added before or after the addition of the labeled gp 120 or derivative and the effect of the antibody on binding can be determined by comparing the degree of binding in that situation against a base line standard with that gp 120 or derivative, not in the presence of the antibody.

A preferred assay uses the labeled gp 120, or derivative portion, for example a gp 120 protein derived from an M-tropic strain such as JR-FL, iodinated using for instance solid phase lactoperoxidase (in one example having a specific activity of 20 $\mu Ci/\mu g$). The cell line containing the chemokine receptor in this example would be a CCR5 cell line, e.g. L1.2 or membranes thereof. Soluble CD4 would be present.

In one embodiment, the conformational envelope polypeptide, such as gp 120 should contain a sufficient number of amino acid residues to define the binding site of the gp 120 to the chemokine receptor (e.g. typically from the V3 loop) and a sufficient number of amino acids to maintain the conformation of the peptide in a conformation that approximates that of wild-type gp 120 bound to soluble CD4 with respect to the chemokine receptor binding site. Preferably, the V1/V2 loops are deleted. In other embodiments at least portions of the V3 loop can be removed to remove masking amino acid residues. In order to maintain the conformation of the polypeptide one can insert linker residues that permit potential turns in the polypeptides structure. For example, amino acid residues such as Gly, Pro and Ala. Gly is preferred. Preferably, the linker residue is as small as necessary to maintain the overall configuration. It should typically be smaller than the number of amino acids in the variable region being deleted. Preferably, the linker is 8 amino acid residues or less, more preferably 7 amino acid residues or less. Even more preferably, the linker sequence is 4 amino acid residues or less. In one preferred embodiment the linker sequence is one residue. Preferably, the linker residue is Gly.

In one preferred embodiment, the gp 120 also contains a CD4 binding site (e.g. from the C3 region residues 368 and 37.0, and from the C4 region residues 427 and 457). The chemokine binding site is a discontinuous binding site that includes portions of the C2, C3, C4 and V3 regions. By deletion of non-essential portions of the gp120 polypeptide—such as deletions of portions of non-essential variable regions (e.g. V1/V2) or portions in the constant regions (e.g. C1, C5) one can increase exposure of the CD4 binding site. Another embodiment is directed to a gp 120 portion containing a chemokine binding site. Similarly, by deleting the non-essential portions of the protein one can increase exposure of the chemokine binding site. The increased exposure enhances the ability to generate an antibody to the CD4 receptor or chemokine receptor, thereby inhibiting viral entry. Removal of these regions is done while requiring the derivative to retain an overall conformation approximating that of the wild-type protein with respect to the native gp 120 binding region, e.g. the chemokine binding region when complexed to CD4. In addition, one can remove glycosylation sites that are disposable for proper folding. Maintaining conformation can be accomplished by using the above-described linker residues that permit potential turns in the structure of the gp 120 derivative to maintain the overall three-dimensional structure. Preferred amino acid residues that can be used as linker include Gly and Pro. Other amino acids can also be used as part of the linker, e.g. Ala. Examples on how to prepare such peptides are described more fully in Wyatt, R., et al. *J. of Virol.* 69:5723–5733 (1995); Thali, M., et al., *J. of Virol.* 67:3978–3988 (1993); and U.S. Pat. No. 5,817,316, issued Oct. 6, 1998 which are incorporated herein by reference. See for example Wyatt which teaches how to prepare V1/V2 deletions that retain the stem portion of the loop.

In one embodiment the gp 120 derivative is designed to be permanently attached at the CD4 binding site to sufficient domains of CD4 to create a conformation of the chemokine binding site approximating that of the native gp 120 CD4 complex.

An alternative gp 120 derivative is one wherein the linkers used result in a conformation for the derivative so that the discontinuous binding site or a discontinuous epitope such as CD4BS or CD4i with the chemokine receptor approximates the conformation of the discontinuous binding site for the chemokine receptor in the wild-type gp 120/CD4 complex. These derivatives can readily be made by the person of ordinary skill in the art based upon the above described methodologies and screened in the assays shown herein to ensure that proper binding is obtained.

The gp 120 polypeptide can also be bound to at least a portion of a gp41 polypeptide, namely the coiled coil. Some of these derivatives will lack the gp41 transmembrane region and will therefore be made as secreted, soluble oligomers. For example, gp41 portions lacking the transmembrane region but retaining the cytoplasmic region, others truncated beginning with the transmembrane region. The gp41 polypeptide contains the indicated cysteine residues, which result in the formation of the SH bonds between the monomers thereby stabilizing the complex as a trimer having spikes similar to that found in the wild type.

These immunogenic oligomers can be used to generate an immune reaction in a host by standard means. For example one can administer the polypeptide in adjuvant. In another approach, a DNA sequence encoding the envelope protein, e.g., the one based upon gp 120 can be administered by standard techniques. The approach of administering the protein is presently preferred.

The protein is preferably administered with an adjuvant. Adjuvants are well known in the art and include aluminum hydroxide, Ribi adjuvant, etc. The administered protein is typically an isolated and purified protein. The protein is preferably purified to at least 95% purity, more preferably at least 98% pure, and still more preferably at least 99% pure. Methods of purification while retaining the conformation of the protein are known in the art. The purified protein is preferably present in a pharmaceutical composition with a pharmaceutically acceptable carrier or diluent present.

DNA sequences encoding these proteins can readily be made. For example, one can use the native gp 160 (or a derivatized gp 120 portion) of any of a range of primate lentiviruses such as HIV-1 strains which are well known in the art and can be modified by known techniques such as deleting the undesired regions such as variable loops and to insert desired coding sequences such as cysteines and linker segments. In addition to DNA sequences based upon existing strains, the codons for the various amino acid residues are known and one can readily prepare alternative coding sequences by standard techniques.

DNA sequences can be used in a range of animals to express the monomer, which then forms into the trimer and generates an immune reaction.

DNA sequences can be administered to a host animal by numerous methods including vectors such as viral vectors, naked DNA, adjuvant assisted DNA catheters, gene gun, liposomes, etc. In one preferred embodiment the DNA sequence is administered to a human host as either a prophylactic or therapeutic treatment to stimulate an immune response, most preferably as a prophylactic. One can administer cocktails containing multiple DNA sequences encoding a range of HIV env strains.

Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred.

These vectors include herpes virus vectors such as a herpes simplex 1 virus (HSV) vector (Geller, A. I. et al. *J. Neurochem* 64: 487 (1995); Lim, F. et al., in *DNA Cloning: Mammalian Systems*, D. Glouer, Ed. (Oxford Univ. Press, Oxford England) (1995); Geller, A. I. et al., *Proc Natl. Acad. Sci. U.S.A.* 90: 7603 (1993); Geller, A. I., et al., *Proc Natl. Acad. Sci USA* 87: 1149 (1990)], adenovirus vectors (LeGal LaSalle et al., *Science* 259: 988 (1993); Davidson, et al., *Nat. Genet* 3: 219 (1993); Yang, et al., *J. Virol.* 69: 2004 (1995)] and adeno-associated virus vectors (Kaplitt, M. G., et al., *Nat. Genet.* 8:148 (1994)].

The DNA sequence can be operably linked to a promoter that would permit expression in the host cell. Such promoters are well known in the art and can readily be selected. Representative examples of such promoters, include a retroviral LTR or SV40 promoter, the *E. coli*. lac or trp, the phage lambda P[L ] promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda P[R], P[L] and trp. Eukaryotic promoters include CMV immediate early, HSV thymidine kinase, early and late SV40, LTRs from retrovirus, and mouse metallothionein-I. Selection of the appropriate vector, polyadenylation sequence and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by a variety of methods including calcium phosphate transfection, DEAE-Dextran mediated transfection, or electroporation (Davis, L., Dibner, M., Battey, I., *Basic Methods in Molecular Biology*, (1986)).

Stabilized forms of these complexes can readily be made, for example, by conjugates such as a poly(alkylene oxide) conjugate. The conjugate is preferably formed by covalently bonding the hydroxyl terminals of the poly(alkylene oxide) and a free amino group in the gp 120 portion that will not affect the conformation of the discontinuous binding site. Other art recognized methods of conjugating these materials include amide or ester linkages. Covalent linkage as well as non-covalent conjugation such as lipophilic or hydrophilic interactions can be used.

The conjugate can be comprised of non-antigenic polymeric substances such as dextran, polyvinyl pyrrolidones, polysaccharides, starches, polyvinyl alcohols, polyacryl amides or other similar substantially non-immunogenic polymers. Polyethylene glycol(PEG) is preferred. Other poly(alkylenes oxides) include monomethoxy-polyethylene glycol polypropylene glycol, block copolymers of polyethylene glycol, and polypropylene glycol and the like. The polymers can also be distally capped with C1–4 alkyls instead of monomethoxy groups. The poly(alkylene oxides) used must be soluble in liquid at room temperature. Thus, they preferably have a molecular weight from about 200 to about 20,000 daltons, more preferably about 2,000 to about 10,000 and still more preferably about 5,000.

One can administer these stabilized compounds to individuals by a variety of means. For example, these antibodies can be included in vaginal foams or gels that are used as preventives to avoid infection and applied before people have sexual contact.

The peptides or antibodies when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 μg/kg a day, more preferably 1 to 10,000 μg/kg.

Routes of administration include oral, parenteral, rectal, intravaginal, topical, nasal, ophthalmic, direct injection, etc.

Changes in the viral envelope glycoproteins, in particular in the third variable (V3) region of the gp 120 exterior envelope glycoprotein, determine tropism-related phenotypes (Cheng-Mayer et al., 1990; O'Brien et al., 1990; Hwang et al., Westervelt et at, 1992; Chesebro et al., 1992; Willey et al., 1994). Amino acid changes in the V3 region (Helseth et al., 1990; Freed et al., 1991; Ivanoff et al., 1991; Bergeron et al., 1992; Grimaila et al., 1992; Page et al., 1992; Travis et al., 1992) and the binding of antibodies to this domain (Putney et al., 1986; Goudsmit et al., 1988; Linsley et al., 1988; Rusche et al., 1988; Skinner et al., Javeherian et al., 1989) have been shown to disrupt a virus entry process other than CD4 binding. Accordingly, one can create derivatives and change the phenotype for a particular receptor by substituting V3 loops.

One can inhibit infection by directly blocking receptor binding. This can be accomplished by a range of different approaches. For example, antibodies. One preferred approach is the use of antibodies to the binding site for these chemoline receptors. Antibodies to these receptors can be prepared by standard means using the stable immunogenic oligomers. For example, one can use single chain antibodies to target these binding sites.

As used herein the inhibition of HIV infection means that as compared to a control situation infection is reduced, inhibited or prevented. Infection is preferably at least 20% less, more preferably at least 40% less, even more preferably at least 50% less, still more preferably at least 75% less, even more preferably at least 80% less, and yet more preferably at least 90% less than the control.

One preferred use of the antibodies is to minimize the risk of HIV transmission. These antibodies can be included in ointments, foams, creams that can be used during sex. For example, they can be administered preferably prior to or just after sexual contact such as intercourse. One preferred composition would be a vaginal foam containing one of the antibodies. Another use would be in systemic administration to block HIV-1 replication in the blood and tissues. The antibodies could also be administered in combination with other HIV treatments.

An exemplary pharmaceutical composition is a therapeutically effective amount of a the oligomer, antibody etc. that for examples affects the ability of the receptor to facilitate HIV infection or for the DNA sequence or the oligomer that can induce an immune reaction, thereby acting as a prophylactic immunogen, optionally included in a pharmaceutically-acceptable and compatible carrier. The term "pharmaceutically-acceptable and compatible carrier" as used herein, and described more fully below, includes (it one or more compatible solid or liquid filler diluents or encapsulating substances that are suitable for administration to a human or other animal, and/or (ii) a system, such as a retroviral vector, capable of delivering the molecule to a target cell. In the present invention, the term "carrier" thus denotes an organic or inorganic ingredient, natural or synthetic, with which the molecules of the invention are combined to facilitate application. The term "therapeutically-effective amount" is that amount of the present pharmaceutical compositions which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic internal after the initial administration. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being commingled with a small molecule, nucleic acid and/or polypeptides of the present invention, and with each other, in a manner such that does not substantially impair the desired pharmaceutical efficacy.

Dose of the pharmaceutical compositions of the invention will vary depending on the subject and upon particular route of administration used. Dosages can range from 0.1 to 100,000 µg/kg per day, more preferably 1 to 10,000 µg/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at 5 months after second dose. See Product Information, Physician's Desk Reference, Merck Sharp & Dohme (1990), at 1442–43. (e.g., Hepatitis B Vaccine-type protocol); (ii) Recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See Product Information, Physidan's Desk Reference, Merck Sharp & Dohme (1990), at 879 (e.g., Diptheria, Tetanus and Pertussis-type vaccine protocols). Desired time intervals for delivery of multiple doses of a particular composition can be determined by one of ordinary skill in the art employing no more than routine experimentation.

The antibodies, DNA sequences or oligomers of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

The compositions include those suitable for oral, rectal, intravaginal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. Methods typically include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The term "antibodies" is meant to include monoclonal antibodies, polyclonal antibodies and antibodies prepared by recombinant nucleic acid techniques that are selectively reactive with polypeptides encoded by eukaryotic nucleotide sequences of the present invention. The term "selectively reactive" refers to those antibodies that react with one or more antigenic determinants on e.g. gp 120 and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes, as well as to block bindiner interactions.

For example, cDNA clone encoding a gp 120 of the present invention may be expressed in a host using standard techniques (see above; see Sambrook et al., Molecular Cloning; A Laboratory Manual, Cold Spring Harbor Press, Cold Spring Harbor, N.Y.: 1989) such that 5–20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Preferably, one would design a stable cell could expressing high levels of the proteins which be selected and used to generate antibodies For example, mice can be immunized twice intraperitoneally with approximately 50 micrograms of protein immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of polypeptides encoded by a eukaryotic nucleotide sequence of the present invention may be analyzed in order to identify desired portions of amino acid sequence which may be associated with receptor binding. For example, polypeptide sequences may be subjected to computer analysis to identify such sites.

For preparation of monoclonal antibodies directed toward polypeptides encoded by a eukaryotic nucleotide sequence of the invention, any technique that provides for the production of antibody molecules by continuous cell lines may be used. For example, the hybridoma technique originally developed by Kohler and Milstein (*Nature*, 256: 495–497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to the resultant antibodies or to other molecules of the invention. See, for example, "Conjugate Vaccines", Contributions to Microbiology and Immunology, J. M. Cruse and R. E. Lewis, Jr (eds), Carger Press, N.Y., (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myasthenia Gravis by toxin-acetylcholine receptor conjugates." Jour. Immun. 133:1335–2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185–216; and Vitetta et al., supra).

Preferred linkers are described in the literature. See, for example, Ramalcrishnan, S. et al., Cancer Res. 44:201–208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimides hydrochloride; (ii) SMPT (4-succinimidyloxycarbonyl-alpha-methyl-alpha-(2-pyridyl-dithio)-toluene (Pierce Chem. Co., Cat. (21558G); (ii) SPDP (succinimidyl-6 (3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Antibodies of the present invention can be detected by appropriate assays, such as the direct binding assay discussed earlier and by other conventional types of immunoassays. For example, a sandwich assay can be performed in which the receptor or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

The following Examples serve to illustrate the present invention, and are not intended to limit the invention in any manner.

To produce recombinant murine C3d we constructed an inducible Drosophila expression vector containing C3d sequences that eliminate the internal thiol by a C to S mutation. We encoded an N-terminal His tag for purification purposes and a thrombin cleavage site to allow cleavage of the tag following purification. The C-terminus is constructed to contain a GGG tail with a terminal C residue to provide an accessible free sulfhydryl (C3d-GGGC). We shuttled the C3d-GGGC sequences into the mammalian expression vector pCDNA3.1 to allow us to transiently express and metabolically label C3d-GGGC to optimize the gp 120 coupling strategy.

We immunized mice with a truncated form of gp 120 ( )82)C5gp 120), either with (( )82)C5gp 120-C3d2) or without C3d ( )82)C5gp 120), to assess the effect of C3d on gp 120 immunogenicity. These immunizations have been performed in the presence of the non-denaturing adjuvant, Ribi (Sigma).

Following the second inoculation, 3 of 4 mice immunized with )82)C5gp 120/Ribi had undetectable levels of gp 120-specific antibodies as determined by ELISA. The fourth mouse in the group displayed a gp 120-specific titer of 1:1,000. By contrast, all four of the animals in the group immunized with )82)C5gp 120-C3d2/Ribi exhibited titers exceeding 1:10,000. Thus, there was a significant enhancement of gp 120 immunogenicity by C3d, when formulated in Ribi adjuvant. These data demonstrate the ability to use the properties of C3d to favorably affect antigen presentation and show that the gp 120-coupled C3d moieties are functional in vivo.

Graphics. Molecular graphics were produced using MidasPlus (University of California, San Francisco) and GRASP.30

Assignment of Variability. Variability in gp 120 residues was assessed using an alignment of sequences derived from approximately 400 HIV-1, HIV-2 and simian immunodeficiency viruses.[49] Residues were assigned variability indices and color coded as follows:

- Red: conserved in all primate immunodeficiency viruses;
- Orange: conserved in all HIV-1, including groups M and O and chimpanzee isolates;
- Yellow: some variation among HIV-1 isolates (divergence from the consensus sequence in 1–8 of the 12 HIV-1 groups examined).
- Green: variable among HIV-1 isolates (divergence from the consensus sequence in, 9 of the 12 HIV-1 groups examined).

Molecular Modeling. Residues 88, 89, and 397–409, which are disordered in the ternary complex crystals,[12] were built manually using the program TOM. For the V4 loop (residues 397–409), a dominant constraint was the distance between the ordered residues 396 and 410 (C—C distance of 26.88 Δ). For the carbohydrate, examination of the N-linked carbohydrate in several crystal structures (e.g. 1fc2, 1gly, 1lte) showed that the core common to both high-mannose and complex N-linked sugars, $(NAG)_2(MAN)_3$, did not differ greatly in conformation after alignment of the first NAG. This core, which represents roughly half the total glycosylation for a typical N-linked site, was built onto each of the 18 consensus N-linked glycosylation sites found on the HXBc2 gp 120 core. The stereochemistry of this initial model was refined using simulated annealing in XPLOR. Briefly, the model was heated to between 2,500° and 3,500° K., and "slow cooled" in steps of 25° to 300° K. At each step, molecular dynamics were performed with the core gp 120 fixed, allowing only the modeled residues and carbohydrate (including any attached Asn) to move. In three separate runs, performing molecular dynamics for 5 fs/step, all steric clashes could be removed and the geometry idealized, with an average root mean square (RMS) of carbohydrate movement of only ~3.5Δ. Four subsequent runs were made using dynamic times of between 50–75 fs/step. The carbohydrate positions obtained from these runs differed more substantially from those in the starting model (average carbohydrate RMS difference of roughly 8Δ). Two of the models from these longer annealings were much more similar to each other than to the rest (RMS differences in carbohydrate of ~4Δ versus ~8Δ for all other models). One had been heated to 3,500° K with dynamics of 75 fs/step. The other (shown in the figures) was heated to only 2,500° K with dynamics of 50 fs/step. In general the RMS movement of the NAG sugars was roughly half the RMS movement of the MAN sugars, reflecting greater conformational flexibility further from the protein surface.

In primary sequence, human and simian immunodeficiency virus gp 120 glycoproteins consist of five variable regions (V1–V5) interposed among more conserved regions.[49] Variable regions V1–V4 form, exposed loops anchored at their bases by disulfide bonds.[50]

Neutralizing antibodies recognize both variable and conserved gp 120 structures. The V2 and V3 loops contain epitopes for strain-restricted neutralizing antibodies.[51-53] More broadly neutralizing antibodies recognize discontinuous, conserved epitopes in three regions of the gp 120 glycoprotein (Table 1). In HIV-1-infected humans, the most abundant of these are directed against the CD4 binding site (CD4BS) and block gp 120-CD4 interaction.[44,45] Less common are antibodies against epitopes induced or exposed upon CD4 binding (CD4i).[54] Both CD4i and V3 antibodies disrupt the binding of gp 120-CD4 complexes to chemokine receptors.[46,47] A third gp 120 neutralization epitope is defined by a unique monoclonal antibody, 2G12,[55] which does not efficiently block receptor binding.[47]

The X-ray crystal structure of an HIV-1 gp 120 core in a ternary complex with two-domain soluble CD4 and the Fab fragment of the CD4i antibody, **17*b*. The gp 120 core lacks the V1/V2 and V3 variable loops, as well as N- and C-terminal sequences, which interact with the gp41 glycoprotein,[43] and is enzymatically deglycosylated.[48,57] Despite these modifications, the gp 120 core binds CD4 and antibodies against CD4BS and CD4i epitopes[57,58] and thus retains structural integrity. The gp 120 core is composed of an inner domain, an outer domain and a third element, the "bridging sheet",[48] (FIG. 3**A). All three structural elements contribute, either directly or indirectly, to CD4 and chemokine receptor binding.[48]

Although generally well-conserved compared with the five variable regions, some variability in the surface of the gp 120 core is evident when the sequences of all primate immunodeficiency viruses are analyzed. This variability is disproportionately associated with the surface of the outer domain proximal to the V4 and V5 regions and removed from the receptor-binding regions (FIGS. 3A–3C). The A, C, D and E surface loops (12) contribute to the variability of this surface. The potential N-linked glycosylation sites present in the gp 120 core are concentrated in this variable half of the protein (FIGS. 3B and 3C). In fact, the only conserved residues apparent on this relatively variable surface are asparagine 356 and threonine/serine 358, which constitute a complex carbohydrate addition site within the E loop (FIGS. 3B and 3C). Since most carbohydrate moieties may appear as "self" to the immune system, the extensive glycosylation of the outer domain surface may render it less visible to immune surveillance. This helps to explain why antibodies directed against this gp 120 surface have been identified so infrequently.

The receptor-binding regions retained in the gp 120 core are well-conserved among primate immunodeficiency viruses.[48] Also highly conserved is the surface of the inner domain spanned by the β1 helix and located opposite the variable surface described above (FIG. 3D). This surface appears to interact with gp41 and/or with N-terminal gp 120 segments absent from the gp 120 core. This inner domain surface and the receptor-binding regions are devoid of glycosylation.

In conjunction with prior mutagenic and antibody competition analyses,[42,43,54,57] the gp 120 core structure reveals for the first time the spatial positioning of the conserved gp 120 neutralization epitopes. Although the major variable loops are either absent (V1/V2 and V3) or poorly resolved (V4) in the gp 120 core structure, their approximate positions can be deduced (FIG. 4A). The conserved gp 120 neutralization epitopes are discussed in relation to these variable loops and to the variable, glycosylated core surface.

a) CD4i epitopes. The gp 120 epitope recognized by the CD4i antibody, 17b, can be directly visualized in the crystallized ternary complex[48] (FIGS. 43 and 4C). Strands from the gp 120 fourth conserved (C4) region and the V1/V2 stem contribute to an antiparallel β-sheet (the "bridging sheet" (see FIG. 3A)) that contacts the antibody. The vast majority of gp 120 residues previously implicated in formation of the CD4i epitopess[54] (Table 1) are located either within this (sheet or in nearby structures. With the exception of Thr 202 and Met 434, the gp 120 residues in contact with the 17b Fab are highly conserved among HIV-1 isolates (FIGS. 3C and 4A). The prominent ("male") CDR3 loop of the 17b heavy chain dominates the contacts with gp 120, with additional contacts through the heavy chain CDR2.[48] Unusually, there are minimal 17b light chain contacts, leaving a large gap between the gp 120 core and most of the 17b light chain surface. In the complete gp 120 glycoprotein, this gap is likely occupied by the V3 loop. This is consistent with the position and orientation of the V3 stem on the gp 120 core structure,[48] the effect of V3 deletions on the binding of CD4i antibodies in the absence of soluble CD4,[58] the competition of some V3-directed antibodies with CD4i antibodies,[42] and the ability of both antibody groups to block chemokine receptor binding.[46,47] The chemokine receptor-binding region of gp 120 appears to consist of elements near or within the "bridging sheet" and the V3 loop (FIG. 3A), a model that is supported by mutagenic analysis.

The V2 loop likely resides on the side of the 17b epitope opposite the V3 loop (FIG. 4A). The V1/V2 loops, which vary from 57 to 86 residues in length,[49] are dispensable for HIV-1 replication,58,63 but decrease the sensitivity of viruses to neutralization by antibodies against V3 and CD4i epitopes.[63] The latter effect is mediated primarily by the V2 loop,[58] suggesting that part of the V2 loop folds back along the V1/V2 stem to mask the "bridging sheet" and adjacent V3 loop. The proximity of the V2 and V3 loops is supported by the observation that, in monkeys infected with simian-human immunodeficiency viruses (SHIVs), neutralizing antibodies are raised against discontinuous epitopes with V2 and V3 components (B. Etemad-Moghadam and J. Sodroski). The CD4i epitopes are apparently masked by the flanking V2 and V3 loops, requiring the evolution of antibodies with protruding ("male") CDRs to access these conserved epitopes. CD4 binding has been suggested to reposition the V1/V2 loops, thus exposing the CD4i epitopes[58] The presence of contacts between the V1/V2 stem and CD4 in the crystal structured is consistent with this model.

b) CD4BS epitopes. CD4 makes a number of contacts within a recessed pocket on the gp 120 surface. The gp 120-CD4 interface includes two cavities, one water-filled and bounded equally by both proteins, the other extending into the gp 120 interior and contacting CD4 only at phenylalanine 43 (FIG. 3A).[48] Table 1 and FIGS. 4B and 4C, show the gp 120 residues implicated in the formation of CD4BS epitopes recognized by eight representative antibodies. CD4BS epitopes are uniformly disrupted by changes in Asp 368 and Glu 370,[56] which surround the opening of the "Phe 43 cavity". These residues are located on a ridge at the intersection of the two receptor-binding gp 120 surfaces, consistent with competition studies suggesting that CD4BS epitopes overlap both the CD4i epitopes and the binding site for CD4.[42,54] The location of the gp 120 residues implicated in the formation of the CD4BS epitopes suggests that important elements of the CD4-binding surface of gp 120 are accessible to antibodies.

Some CD4BS antibodies, like IgG1b12, are particularly potent at neutralizing HIV-l59 IgG1b12 binding is disrupted by gp 120 changes that affect the binding of other CD4BS antibodies but, atypically, is sensitive to changes in the V1/V2 stem-loop structured The observation that some well-conserved residues in the gp 120 V1/V2 stem contact CD44[8] raises the possibility that this protruding structure also contributes to the IgG1b12 epitope. This might increase the ability of the antibody to access the assembled envelope glycoprotein triter, thus increasing neutralizing capability.

While the CD4BS epitopes and the CD4-binding site overlap, several observations demonstrate that the binding of CD4BS antibodies differs from that of CD4. Changes in Trp 427, a gp 120 residue that contacts both the "Phe 43 cavity" and CD4, uniformly disrupt CD4 binding but affect the binding of only some CD4BS antibodies (Table 1). Conversely, some changes in other cavity-lining gp 120 residues, Ser 256 and Thr 257, affect the binding of CD4BS antibodies more than the binding of CD4.t Since the recessed position of Ser 256 and Thr 257 in the current crystal structure (FIGS. 4B and 4C) makes direct contacts with antibody unlikely, either the effects of changes in these residues are indirect or the CD4BS antibodies recognize a gp 120 conformation that differs from the CD4-bound state. With respect to the latter possibility, several of the residues implicated in the integrity of the CD4BS epitopes are located in the interface between the inner and outer gp 120 domains. CD4BS antibodies might recognize a gp 120 conformation in which the spatial relationship between the domains is altered compared with the CD4-bound state, thus allowing better surface exposure of these residues. Differences between the CD4BS epitopes and the CD4-binding site create opportunities for neutralization escape.[56] The gp 120 residues surrounding the "Phe 43" cavity are highly conserved among primate immunodeficiency viruses (FIG. 4A), but the observed modest variation in adjacent surface-accessible residues (e.g., Pro 369, Thr 373 and Lys 432) can account for decreased recognition of the gp 120 glycoprotein from some geographic clades of HIV-1 by CD4BS antibodies.[60] Additional potential for variation near or within the CD4BS epitopes is created by the unusual water-filled cavity in the gp 120-CD4 binding interface, since CD4 binding can apparently tolerate change in the gp 120 residues contacting this cavity.[48]

The recessed nature of the CD4 binding pocket on gp 120 (FIG. 3C) can delay the generation of high-affinity antibodies against the CD4BS epitopes and may afford opportunities to mining the antiviral efficacy of such antibodies once they are elicited. The degree of recession is probably much greater on the full-length, glycosylated gp 120 than is evident on the crystallized gp 120 core. The recessed pocket is flanked on one side by the V1/V2 stem-loop structure. The characterization of HIV-1 escape mutants from the IgG1b12 CD4BS antibody and the mapping of several V2 conformational epitopes support a model in which the V2 loop folds back along the V1/V2 stem, with V2 residues 183–188 proximal to Asp 368 and Glu 370. This model is consistent with observations that V1/V2 changes, in combination with V3 changes, can alter the exposure of the adjacent CD4BS epitopes, particularly on the assembled trimer.[64] The high temperature factors associated with the V1/V2 stems imply flexibility in this protruding element (FIGS. 3C and 3D), expanding the potential range of space occupied by the V1/V2 stem-loop structure. This could enhance masking of the adjacent CD4BS and CD4i gp 120 epitopes and divert antibody responses towards the variable loops.

Glycosylation can modify the interaction of antibodies with CD4BS epitopes. The D loop, on the rim of the CD4-binding pocket opposite the V1/V2 stem, contains a well-conserved glycosylation site, asparagine 276 (FIG. 3C). Changes in this site and at the adjacent alanine 281 have been associated with escape from the neutralizing activity of patient sera[61] and have been seen in SHIVs extensively passaged in monkeys.[62] Another conserved glycosylation site at asparagine 386 lies adjacent to both CD4BS and CD4i epitopes (FIG. 3C) and could diminish antibody responses against those sites. Additionally, in various HIV-1 strains, carbohydrates are added to the V2 loop segment (residues 186–188) thought to be proximal to the CD4BS epitopes.

c) The 2G12 epitope. The integrity of the 2G12 epitope is disrupted by changes in gp 120 glycosylation, either by glycosides treatment or mutagenic alteration of specific N-linked carbohydrate addition sites.[19] These sites are located on the relatively variable surface of the gp 120 outer domain, opposite to and approximately 25 Å away from the CD4 binding site (FIGS. 4B and 4C). The gp 120 glycoprotein synthesized in mammalian cells exhibits a dense concentration of high-mannose sugars in this region (FIG. 4a). Even in the enzymatically deglycosylated gp 120 core, carbohydrate residues constitute much of this surface. 2G12 likely binds at least in part to these carbohydrates, explaining the surprising conservation of the 2G12 epitope despite the variability of the underlying protein surface, which includes the stem of the V3 loop and the V4 variable region. The inclusion of carbohydrate in the epitope might also explain the apparent rarity with which these antibodies are generated. The localization of the 2G12 epitope is consistent with previous studies indicating that 2G 12 forms a unique competition group[42,46] and does not interfere with the binding of monomeric gp 120 to either CD4 or chemokine receptors.[47] Since the 2G12 epitope is predicted to be oriented towards the target cell upon CD4 binding (see below), the antibody may sterically impair interactions of the oligomeric envelope glycoprotein complex with host cell moieties.

Because antibodies directed to the heavily glycosylated surface containing the 2.612 epitope are very rare, we have also explained how to unmask the immunogenicity of this immunological silent region. The modified molecule will contain pan-reactive T-cell helper epitopes (Alexander, et al., *Immunity, Vol.* 1, 751–761 (1994)). Previous studies have demonstrated the ability of helper epitopes to overcome immunological tolerance to self proteins. Thus, immunogenicity will be enhanced by the modified gp 120 genetically incorporating such helper epitope into the self protein. These epitopes are known in the art.

Figure 5:
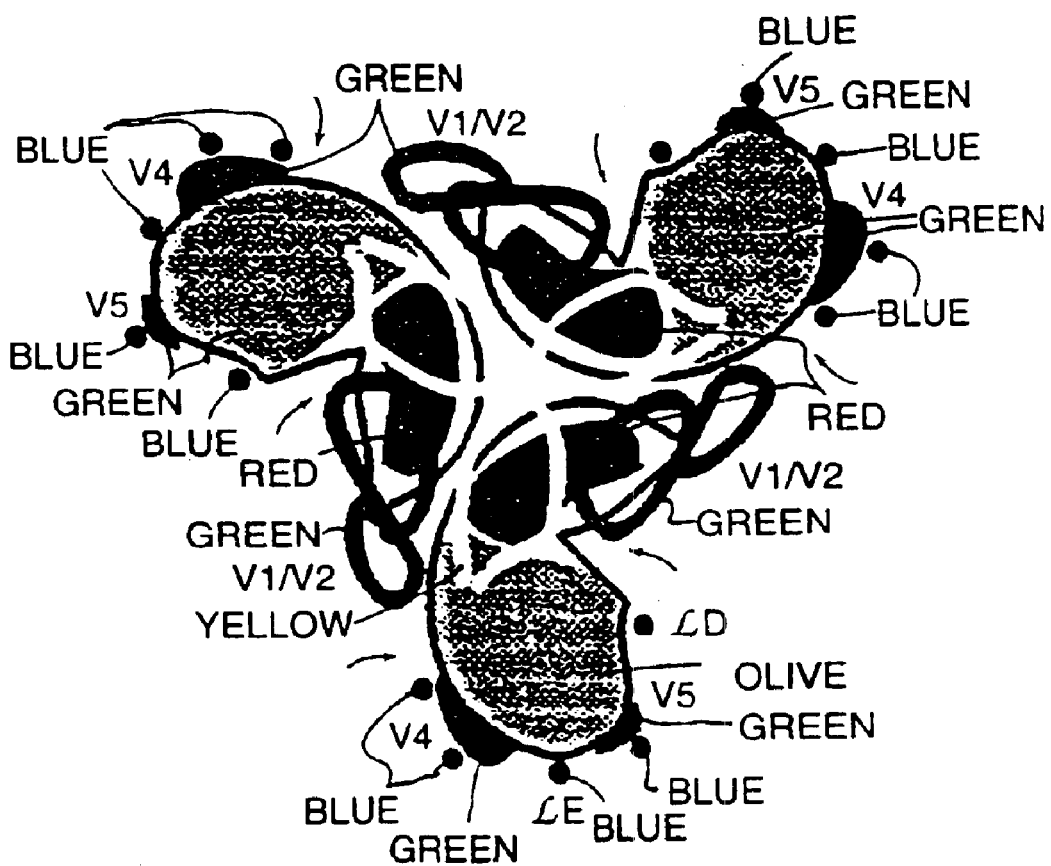

Possible orientations of the exterior glycoproteins in the trimer are significantly constrained by the requirement that observed and deduced binding sites for receptors and neutralizing antibodies, sites of N-linked glycosylation, and variable structures be exposed on the surface of the assembled complex. The two-domain CD4 in the ternary complex structure was aligned to the structure of four-domain CD429 to orient the trimer model with respect to the target cell membrane. The consequences of such a model, which is shown in FIG. 5, are: a) the chemokine receptor-binding sites are clustered at the vertex of the trimer predicted to be closest to the target cell; b) both variable and conserved neutralization epitopes are concentrated on the half of gp 120 facing the target cell; c) possibilities for intersubunit interactions among the variable structures that could help mask conserved neutralization epitopes are created; d) the subset of gp 120 glycosylation sites to which complex carbohydrates are added in mammalian cells[14] is well-exposed on the outer periphery of the trimer; e) the highly conserved surface near the β1 helix is available for gp41 and/or gp 120 protein interactions within the trimers; and f) the surface of the assembled envelope glycoprotein complex is roughly hemispherical, thus minimizing the surface area of the viral spike that is potentially exposed to antibodies. In summary, the X-ray crystal structure of the gp 120 core/two-domain CD4/17*b* Fab complex provides a framework for visualizing key interactions between HIV-1 and the humoral immune system. Previous antibody competition analyses suggested that the gp 120 surface buried in the assembled trimer elicits non-neutralizing antibodies.[56] By contrast, the binding sites for neutralizing antibodies cluster on a different gp 120 surface. Our structural studies support the existence of non-neutralizing and neutralizing faces of gp 120, and reveal another, immunologically "silent" face of the glycoprotein (FIG. 4D). This outer domain surface, along with the major variable loops, contributes to the large fraction of the gp 120 surface that is protected against antibody responses by a dense array of carbohydrates and by the capacity for variation. Although the variability and orientation of much of this surface may present difficulty in the elicitation of broadly-neutralizing antibodies, by modifying a polypeptide as taught herein, one can unmask the immunological silence of this region and also incorporate, of T-cell helper epitopes into the gp 120 glycoprotein to enhance immunogenicity. The conserved receptor-binding regions of gp 120 represent attractive targets for immune intervention. However, the elicitation of antibodies against these conformation-dependent structures in the wild type protein is inefficient. Since the gp 120 epitopes near the receptor-binding regions span the inner and outer domains, interdomain conformational shifts may decrease their representation in the immunogen pool. The recessed nature of the CD4-binding site likely contributes to its poor immunogenicity. The sequential recognition of two receptors by primate immunodeficiency viruses allows the conserved elements of the chemokine receptor-binding site to be created or exposed only after CD4 binding has occurred, but the proximity of the chemokine-receptor binding site to the cell membrane apparently sterically limits antibody binding. Our modified polypeptide can generate antibodies that more effectively deal with this problem.

21. K. Steimer et al., *Science*, 254:105–108 (1991).
22. M. Posner et al., *J. Immunol.*, 146:4325–4332 (1991).
23. J. Robinson et al., *AIDS Res. Hunt Retro*, 6:567–580 (1990).
24. S. Tilley et al., *Res. Virol.*, 142:247–259 (1991).
25. D. Ho et al., *J. Virol.*, 65:489–493 (1991).
26. M. Thali et al., *J. Virol.*, 67:39783988 (1993).
27. R. Wyatt et al., *J. Virol.*, 69:5723–5733 (1995).
28. R. Wyatt et al., *J. Virol.*, 67:4557–4565 (1993).
29. N. Sullivan et al., *J. Virol.*, 69:4413–4422 (1995).
30. A. Trkola et al., *Nature*, 384:184–186 (1996).
31. C. Rizzuto et al., Identification of a Conserved Human Immunodeficiency Virus gp 120 Glycoprotein Structure Important for Chemokine Receptor Binding, manuscript in preparation.

TABLE 1

Conserved Epitopes for Neutralizing Antibodies Identified on the gp120 Core

| Competition Group | Examples of Monoclonal Antibodies | gp120 Amino Acids[b] | Probable Mechanism of Virus Neutralization | Characteristics | Selected References |
|---|---|---|---|---|---|
| CD4-Binding Site (CD4BS) | F105, 15e, 21h, 1125h, 448D, 39.3, IgG1b12, 830D | Asn88 (13), Asp113 (50), Lys117 (25), Ser256 (75), Thr257 (75), Asn262 (63), Ala266 (13), Asp368 (100), Glu370 (100), Tyr384 (13), Lys421 (50), Trp427 (25), Asp457 (13), Pro470 (25), Asp474 (13), Met475 (13), Asp477 (63), Asp/Leu/Tyr 482/483/484 (25) | Interference with gp120-CD4 binding | CD4BS antibodies complete with CD4 and with antibodies against CD4i epitopes | 8, 9, 20 |
| CD4-induced Epitopes (CD4i) | 17b, 48d | Asn88, Lys117, Lys121, Lys207, Ser256, Thr257, Asn262, ΔV3, Glu370, Glu381, Phe382, Arg419, Ile420, Lys421, Gln422, Ile423, Trp427, Tyr435, Pro438, Met475 | Interference with chemokine receptor binding | CD4 binding increases exposure of the epitopes as a result of movement of the V2 variable loop | 18 |
| 2G12 | 2G12 | Asn295, Thr297, Ser334, Asn386, Asn392, Asn397 | Unknown | Antibody binding is dependent upon proper N-linked glycosylation | 19 |

[a]The gp120 competition groups are defined as in Reference 5.
[b]The gp120 amino acids are numbered according to the sequence of the HXBc2 (IIIB) gp120 glycoprotein, where residue 1 is the methionine at the amino-terminus of the signal peptide. Changes in the amino acids listed resulted in significant reduction in antibody binding to the gp120 glycoprotein (Ref. 18–20). The numbers in parentheses indicate the percentage of the CD4BS antibodies examined whose binding is decreased by changes in the indicated residue.

1. A. Dalgleish et al., *Nature*, 312:763–767 (1984).
2. D. Klakmann et al., *Nature London*, 312:767–768 (1984).
3. L. Lasky et al., *Cell*, 50:975–985 (1987).
4. P. Earl et al., *Proc Natl. Acad. Sci USA*, 87:648–652 (1990).
5. A. Pinter et al., *J. Virol.*, 63:2674–2679 (1989).
6. M. Lu et al., *Nature Structural Biol.*, 2:1075–1082 (1995).
7. D. Chan et al., *Cell*, 89:263–273 (1997).
8. Y. Feng et al., *Science* 272:872–877 (1996).
9. H. Choe et al., *Cell*, 85:1135–1148 (1996).
10. B. Doranz et al., *Cell*, 85:1149–1158 (1996).
11. T. Draoic et al., *Nature*, 381 :667–673 (1996).
12. H. Deng et al., *Nature*, 381:661–666 (1996).
13. G. Alkhatib et al., *Science* 272:1955–1958 (1996).
14. L. Wu et al., *Nature*, 384:179–183 (1996).
15. E. Emini et al., *Nature*, 355:728–730 (1992).
16. S. Putney et al., *Science*, 234:1392–1395 (1986).
17. C. Bruck et al., *Colloque des Cent Garde*, 227–233 (1990).
18. P. Berman et al., *Nature*, 345:622–625 (1990).
19. W. Robey et al., *Pros Natl. Acad. Sci U.S.A.*, 83:7023–7027 (1986).
20. J. Rusche et al., *Proc. Natl. Acad. Sci. U.S.A.*, 85:3198–3202 (1988).
32. A. Benjouad et al., *J. Virol.*, 66:2473–2483 (1992).
33. A. Bolmstedt et al. *JAIDS*, 12:213–220 (1996).
34. G. Gram et al., *Arch Virol.*, 139:253–261 (1994).
35. N. Back et al., *Virology*, 199:431–438 (1994).
36. W. Lee et al., *Proc. Natl. Acad. Sci. USA*, 189:2213–2217 (1992).
37. P. Dempsey et al., *Science*, 217:348–350 (1996).
38. G. Myers et al., Human retroviruses and AIDS: A compilation and analyses of nucleic acid and amino acid sequences. Los Alamos National Laboratory, Los Alamos, N. Mex. (1994).
39. E. Helseth et al., *J. Virol.*, 64:2416–2420 (1990).
40. H. Ditzel et al., *J. Mol. Biol.*, 267:68695 (1990).
41. S. Chamow et al., *J. Biol. Chem.*, 267:15916–15922 (1992).
42. J. Moore et al., *J. Virol.*, 70:1863–1872.(1996).
43. R. Wyatt et al., *J. Virol.*, 71: 9722–9731 (1997).
44. M. Posner et al., *J Immunol.*, 146:4325–4332 (1991).
45. D. Ho et al. *J. Virol.*, 65:489–493 (1991).
46. L. Wu et al. *Nature*, 384:179–183 (1996).
47. A. Trkola et al., *Nature*, 384:184–187 1996).
48. P. Kwong et al., *Nature*, submitted.

49. G. Myers et al., Human retroviruses and AIDS. A compilation and analysis of nucleic acid and amino acid sequences. Los Alamos National Laboratory. Los Alamos, N. Mex. 1996.
50. C. Leonard et al., *J. Biol. Chem.*,265:10373–10382 (1990).
51. M. Fung et al., *J. Virol.*, 66:848–856 (1992).
52. S. Putney et al., *Science*, 234:1392–1395 (1986).
53. J. Rusche et al., *Proc. Natl. Acad. Sci. USA*, 85:3198–3202 (1988).
54. M. Thali et al., *J. Virol.*, 67:3978–3988 (1993).
55. A. Trkola et al., *J. Virol.*, 70:1100–1108 (1996).
56. M. Thali et al., *J. Virol.*, 66:5635–5641 (1992).
57. J. Binley et al., *AIDS Res. Hum. Retroviruses*, 14:191–198 (1998)
58. R. Wyatt et al., *J. Virol.*, 69:5723–5733 (1995).
59. P. Roben al., *J. Virol.*, 68:4821–4828(1994).
60. J. Moore et al., *J. Virol.*, 68:8350–8364 (1994).
61 B. Watkins et al., *J. Virol.*, 67:7493 (1993).
62. G. Karlsson et al., *J. Virol.*, 71:4218 (1997).
63. J. Cao et al., *J. Virol.*, 71:9808–9812 (1997).
64. R. Wyatt et al., *J. Virol.*, 4557–4565 (1993).

All references described herein are incorporated herein by reference.

We claim:

1. A modified gp 120 polypeptide comprising modifications in at least two conserved regions of an envelope protein selected from a primate lentivirus, wherein at least two of the four glycosylation sites in theses regions proximal to the CD4 binding site or CCR5 or CXCR4 chemokine receptor binding site have been altered, wherein the glycosylation sites are selected from the group of amino acids that correspond to positions 197, 276, 301 and 386 of HIV-1 strain HXBc2, wherein the alteration prevents glycosylation at said sites, and wherein the modified polypeptide maintains the overall 3-dimensional structure of a discontinuous conserved epitope of the wild-type gp 120, wherein the discontinuous conserved epitope is a CD4bs epitope or a CD4i epitope, and wherein the gp 120 protein is selected from the group consisting of HIV-1, HIV-2 and SIV.

2. A modified gp 120 polypeptide comprising modifications in at least two conserved regions of an envelope protein selected from a primate lentivirus, wherein at least two of the four glycosylation sites in these regions proximal to the CD4 binding site or CCR5 or CXCR4 chemokine receptor binding site have been altered, wherein the alteration prevents glycosylation at said sites, and wherein the modified polypeptide maintains the overall 3-dimensional structure of a discontinuous conserved epitope of the wild-type gp 120, wherein the discontinuous conserved epitope is a CD4bs epitope or a CD4i epitope, wherein the gp 120 protein is HIV-1 and the glycosylation sites are selected from the group of amino acids that correspond to positions 197, 276, 301 and 386 of HIV-1 strain HXBc2.

3. The modified gp 120 polypeptide of claimed 2, wherein the gp 120 polypeptide further contains at least one of the following changes relative to the wild-type to gp 120 protein:
   (a) introduction of disulfide bonds;
   (b) filling a cavity of the gp 120 protein with hydrophobic amino acid residues;
   (c) introducing a Pro residue at a defined turn structure; or
   (d) increasing the hydrophobicity across the interface between the gp 120 domains.

4. The modified gp 120 polypeptide of claim 3, wherein the polypeptide further contains at least one pan-reactive T-cell helper epitopes.

5. The modified gp 120 polypeptide of claims 2 or 3, wherein one of the glycosylation sites that have been altered corresponds to position 301 of HIV-1 strain HXBc2.

6. The modified gp 120 polypeptide of claims 2 or 3, wherein all four of the glycosylation sites have been altered.

7. The modified gp 120 polypeptide of claim 1, wherein the polypeptide further contains at least one pan-reactive T-cell helper epitopes.

8. The modified gp 120 polypeptide of claim 3, wherein the cavity of the gp 120 protein with hydrophobic amino acid residues corresponds to position Phe43 of HIV-1 strain HXBc2.

9. The modified gp 120 polypeptide of claim 3, wherein the defined turn structure is located at loops selected from the group consisting of V1/V2, V3, V4, V5, £A, £C, and £E loops.

10. The modified gp 120 polypeptide of claim 3, wherein the gp 120 domains are selected from the inner domain, the outer domain and the bridging domain.

11. The modified gp 120 polypeptide of claim 1, wherein at least two conserved regions of an envelope protein are present.

12. The modified gp 120 polypeptide of claim 11, wherein the gp 120 protein is the HIV-1 gp 120.

13. The modified gp 120 polypeptide of claim 11, wherein exposure of the CD4 binding site is increased by deletions of the group of regions consisting of portions of variable region 1, variable region 2, constant region 1 and constant region 5.

* * * * *